(12) United States Patent
Marck et al.

(10) Patent No.: US 7,750,185 B2
(45) Date of Patent: Jul. 6, 2010

(54) PHOTOACTIVE MATERIALS

(75) Inventors: Guy Marck, Schlierbach (FR); Olivier Muller, Lautenbach (FR)

(73) Assignee: Rolic AG, Zug (CH)

( * ) Notice: Subject to any disclaimer, the term of this patent is extended or adjusted under 35 U.S.C. 154(b) by 519 days.

(21) Appl. No.: 10/522,523

(22) PCT Filed: Jul. 25, 2003

(86) PCT No.: PCT/CH03/00507

§ 371 (c)(1), (2), (4) Date: Jan. 26, 2005

(87) PCT Pub. No.: WO2004/013086

PCT Pub. Date: Feb. 12, 2004

(65) Prior Publication Data

US 2005/0288480 A1     Dec. 29, 2005

(30) Foreign Application Priority Data

Jul. 30, 2002   (EP) .................................. 02405659

(51) Int. Cl.
*C08G 69/08* (2006.01)

(52) U.S. Cl. ....................... 564/305; 564/307; 564/315; 528/310

(58) Field of Classification Search .............. 526/303.1; 428/1.26; 564/305, 307, 315
See application file for complete search history.

(56) References Cited

U.S. PATENT DOCUMENTS

| | | | | |
|---|---|---|---|---|
| 4,725,342 | A | * 2/1988 | Crabtree et al. | ........ 204/157.15 |
| 6,139,927 | A | * 10/2000 | Takao et al. | ................. 428/1.26 |
| 6,303,742 | B1 | 10/2001 | Okada | |
| 6,746,730 | B1 | 6/2004 | Tanioka et al. | |
| 2004/0138394 | A1* | 7/2004 | Buchecker et al. | ....... 526/303.1 |

FOREIGN PATENT DOCUMENTS

| | | |
|---|---|---|
| JP | 10195296 A | 7/1998 |
| JP | 10232400 A | 9/1998 |
| WO | WO 99/15576 A1 | 4/1999 |
| WO | WO 99/49360 A1 | 9/1999 |
| WO | WO 00/59966 A1 | 10/2000 |
| WO | 01/00732 A1 | 1/2001 |
| WO | WO 01/53384 A1 | 7/2001 |
| WO | WO 02/053609 A1 | 7/2002 |
| WO | WO 02/054140 A2 | 7/2002 |

OTHER PUBLICATIONS

USPTO Structure search report.*
Schorr M. et al. : "Carbonsäurepiperazide mit chemotherapeutischer Wirkung genen Dicrocoelium dendriticum" Arzeimittel Forschung. Drug Research., vol. 14, No. 10, 1964, pp. 1151-1156, XP002223712.
Database Crossfire Beilstein 'Online! Beilstein Institut zur Förderung der Chemischen Wissenschaften, Frankfurt am Main, DE; XP002223713 & Chem. Ber., vol. 55,1922, p. 722.
Database Crossfire Beilstein 'Online! Beilstein Institut zur Förderung der Chemischen Wissenschaften, Frankfurt am Main, DE; XP002223714 & C. R. Hebd. Seances Acad. Sci., vol. 157, 1913. p. 941.
Database Crossfire Beilstein 'Online! Beilstein Institut zur Förderung der Chemischen Wissenschaften, Frankfurt am Main, DE; XP002223715 & J. Prakt. Chem., vol. 125, 1930, p. 211.
Database Crossfire Beilstein 'Online! Beilstein Instutut zur Förderung der Chemischen Wissenschaften, Frankfurt am Main DE; XP002223716 & Chem. Ber., vol. 20, 1887, p. 441.
Database Crossfire Beilstein 'Online! Beilstein Institut zur Förderung der Chemischen Wissenschaften, Frankfurt am Main, DE; XP002223717 & J. Prakt. Chèm., vol. 125, 1930, p. 301.
Database Crossfire Beilstein 'Online! Beilstein Institut zur Förderung der Chemishen Wissenschaften, Frankfurt am Main, DE; XP002223718 & Gazz. Chim. Ital., vol. 35, 1905, p. 130.
Database Cross Fire Beilstein 'Online ! Beilstein Institut zur Forderung der Chemischen Wissenschaften, Frankfurt am Main, DE; XP002223719 & J. Prakt. Chem., vol. 125, 1930, p. 211.
Martin Schadt, et al., "Surface-Induced Parallel Alignment of Liquid crystals by Linearly Polymerized Photopolymers",Japan Journal of Applied Physics, vol. 31, 1992, Pt. 1, No. 7, pp. 2155-2164.

* cited by examiner

*Primary Examiner*—James Seidleck
*Assistant Examiner*—Gregory Listvoyb
(74) *Attorney, Agent, or Firm*—Sughrue Mion, PLLC

(57) ABSTRACT

Diamine compounds, which in particular are useful as precursors for the production of liquid crystal alignment layers, represented by general formula (I), wherein $A^1$ represents an organic group of 1 to 40 carbon atoms; $A^2$ represents a hydrogen atom or an organic group of 1 to 40 carbon atoms.

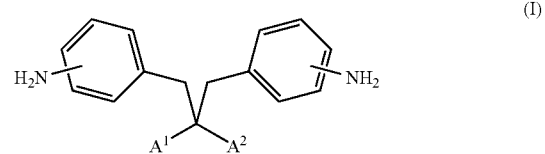

(I)

33 Claims, No Drawings

PHOTOACTIVE MATERIALS

The present invention relates to new diamine compounds and their use as precursors for the production of liquid crystals alignment layers as well as polymers prepared thereof as polymer layers such as orientation layers for liquid crystals and the construction of unstructured and structured optical elements and multi-layer systems.

The successful functioning of a liquid crystal device depends on the ability of the liquid crystal molecules within that device to adopt and maintain an imposed alignment. Alignment of the liquid crystal molecules is achieved by use of an orientation layer which defines a direction of orientation for the liquid crystal molecules of the device with the result that the molecules become aligned with the direction of orientation defined by the orientation layer. In addition to this directional alignment, the orientation layer is also able to impart to the liquid crystal molecules an angle of tilt so that the molecules align themselves at an angle to the surface of the orientation layer rather than lying parallel thereto.

Methods of preparing orientation layers for liquid crystal materials are well known to a skilled person. Customarily used uniaxially rubbed polymer orientation layers such as, for example, polyimides however impact a series of disadvantages like dust generation during the rubbing process and destruction of the thin film transistors. Scratches due to brushing are another problem, which becomes particularly evident when the pixels are of the order of 10 micrometers or less as for instance in microdisplays. Furthermore, the rubbing process does not allow the production of structured layers. Alternatively, orientation layers in which the direction of orientation can be predetermined by irradiation with polarized light avoid the problems inherent to the rubbing process. In addition, it is possible to provide areas having different orientation and tilt and thus to structure the orientation layer as described for example in Jpn. J. Appl. Phys., 31 (1992), 2155-2164 (Schadt et al.).

Photoactive materials for the orientation layers were also described for example in WO-A-99/49360 (Rolic AG), JP-A-10-195296, JP-A-10-232400 (both Samsung Electron Devices Co., Ltd.), WO-A-99115576 (Rolic AG) and WO-A-99/51662 (Kanegafuchi Kagaku Kogyo KK). Orientation layers comprising materials described in these publications, however, have the disadvantage that for certain applications, particularly when used in LCoS liquid crystal displays, a long exposure to light of high intensity may have a degradation effect, which in turn may lead to an undesirable reduction of the resistivity or "holding ratio" of the adjacent liquid crystal mixture. Low holding ratio values mean changes in brightness and contrast over time and thus a disadvantageous deterioration of the viewing characteristics, such as unstable graduations of the grey tones, of a display.

Applicants have now discovered a new class of diamine compounds that can be used in the production of polymer layers, in particular orientation layers for liquid crystals and in the construction of unstructured and structured optical elements and multi-layers systems. These novel diamine compounds show very low light absorbance for wavelengths above 360 nanometer and improved light stability, which leads to reduced or possibly suppressed degradation by visible light of a layer, such as a liquid crystal orientation layer, containing said compounds. Furthermore, the liquid crystal orientation layers made from the materials simultaneously show very good alignment uniformity, excellent voltage holding ratios and reduced image-sticking phenomena.

A first aspect of the present invention provides diamine compounds, which in particular are useful as precursors for the production of liquid crystal alignment layers, represented by the general formula I:

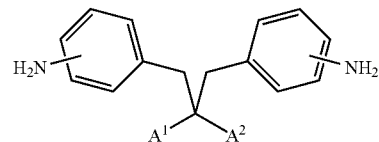

I wherein
$A^1$ represents an organic group of 1 to 40 carbon atoms;
$A^2$ represents a hydrogen atom or an organic group of 1 to 40 carbon atoms.

Preferably, $A^1$ and $A^2$ each independently represent a cyclic, straight-chain or branched alkyl residue which is unsubstituted, mono-substituted by cyano or fluorine, chlorine, or poly-substituted by fluorine or chlorine, having 1 to 40 carbon atoms, wherein one or more —$CH_2$— groups may independently be replaced by a group B, with the proviso that oxygen atoms are not directly attached to each other, wherein B represents a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O— and —$Si(CH_3)_2$—O—$Si(CH_3)_2$— and wherein $R^1$ represents a hydrogen atom or lower alkyl.

Further, $A^1$ and $A^2$ each independently preferably represent a mesogen group represented by general formula II:

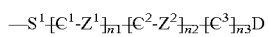

II wherein
$C^1$ to $C^3$ each independently represent an aromatic or an alicyclic group, which is unsubstituted or mono- or poly-substituted by a cyano group or by halogen atoms, or by a cyclic, straight-chain or branched alkyl residue which is unsubstituted, mono- or poly-substituted by fluorine, chlorine, having 1 to 18 carbon atoms, wherein one or more non-adjacent —$CH_2$— groups may independently be replaced by a group B;
D represents a hydrogen atom, a halogen atom, a cyano group, or a straight-chain or branched alkyl residue which is unsubstituted, mono-substituted by cyano or fluorine, chlorine, or poly-substituted by fluorine, chlorine, having 1 to 24 carbon atoms, wherein one or more non-adjacent —$CH_2$— groups may independently be replaced by a group B, or represents a organic group having a steroid skeleton;
$S^1$ represents a single bond or a spacer unit such a straight-chain or branched alkylene group which is unsubstituted, mono or poly-substituted by a cyano group or by halogen atoms, having 1 to 24 carbon atoms, wherein one or more non-adjacent —$CH_2$— groups may independently be replaced by a group B;
$Z^1$, $Z^2$ each independently of the other represent a single bond or a spacer unit such a straight-chain or branched alkylene group which is unsubstituted, mono or poly-substituted by a cyano group or by halogen atoms, having 1 to 8 carbon atoms, wherein one or more non-adjacent —$CH_2$— groups may independently be replaced by a group B;
n1 to n3 are each independently 0 or 1; and
B is as defined above, with the proviso that if n1=n2=n3=0 then D is a straight-chain or branched alkyl residue which is unsubstituted, mono-substituted by cyano or fluorine, chlorine, or poly-substituted by fluorine, chlorine, having 5 to 24 carbon atoms, wherein one or more non-adjacent —$CH_2$— groups may independently be replaced by a group B, or represents a organic group having a steroid skeleton.

It is preferred that groups $C^1$ to $C^3$ are selected from pyrimidine-2,5-diyl, pyridine-2,5-diyl, 1,4- or 2,6-naphthylene, decahydronaphthalin-2,6-diyl, 1,2,3,4-tetrahydronaphtalin-2,6-diyl, cyclohexane-1,4-diyl and phenylene, which is unsubstituted or substituted by a cyclic, straight-chain or branched alkyl residue which is unsubstituted, mono- or poly-substituted by fluorine, chlorine having from 1 to 12 carbon atoms in which optionally one or more non-adjacent —$CH_2$— groups are replaced by —O—, —CO—, —CO—O—, —O—CO—, —CH=CH— and —C≡C—.

It is especially preferred that groups $C^1$ to $C^3$ are selected from cyclohexane-1,4-diyl and phenylene, which is unsubstituted or substituted by a cyclic, straight-chain or branched alkyl residue having 1 to 12 carbon atoms in which optionally one or more non-adjacent —$CH_2$— groups are replaced by —O—, —CO—, —CO—O—, —O—CO—, —CH=CH— and —C≡C—.

It is preferred that D is a hydrogen atom, a fluoro atom, a chloro atom, a cyano group or a straight-chain or branched alkyl residue which is unsubstituted, mono-substituted by cyano or fluorine, chlorine, or poly-substituted by fluorine, chlorine, having 1 to 18 carbon atoms, wherein one or more non-adjacent-$CH_2$— groups may independently be replaced by —O—, —CO—, —CO—O—, —O—CO—, —$NR^1$—CO—, —CO—$NR^1$—, —$NR^1$—CO—O—, —O—CO—$NR^1$—, —CH=CH—, —C≡C— and —O—CO—O—, wherein $R^1$ represents a hydrogen atom or lower alkyl, or represents an organic group having a steroid skeleton.

It is especially preferred that D is a hydrogen atom, a fluoro atom, a chloro atom, a cyano group or a straight-chain or branched alkyl residue, having 1 to 12 carbon atoms, wherein one or more non-adjacent —$CH_2$— groups may independently be replaced by —O—, —CO—, —CO—O—, —O—CO—, —CH=CH—, —C≡C— and —O—CO—O—.

It is preferred that the group $S^1$ is selected from a single covalent bond, —CO—O—, —CO—$NR^1$—, —CO— and a straight-chain or branched alkylene group which is unsubstituted, mono or poly-substituted by fluorine, chlorine and cyano, having 1 to 14 carbon atoms, wherein one or more non-adjacent —$CH_2$— groups may independently be replaced by a group B, wherein $R^1$ represents a hydrogen atom or lower alkyl.

It is more preferred that $S^1$ is selected from a single covalent bond, —CO—O—, —CO—, —$(CH_2)_r$—, —$(CH_2)_r$—O—, —$(CH_2)_r$—CO—, —$(CH_2)_r$—CO—O—, —$(CH_2)_r$—O—CO—, —$(CH_2)_r$—CO—$NR^1$—, —$(CH_2)_r$—$NR^1$—CO—, —$(CH_2)_r$—$NR^1$—, —CO—O—$(CH_2)_r$—, —CO—$NR^1$—$(CH_2)_r$—, —CO—O—$(CH_2)_r$—O—, —CO—$NR^1$—$(CH_2)_r$—O—, —CO—$NR^1$—$(CH_2)_r$—$NR^1$—, —CO—$NR^1$—$(CH_2)_r$—O—CO—, —$(CH_2)_r$—O—$(CH_2)_s$—, —$(CH_2)_r$—CO—O—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$—CO—O—$(CH_2)_s$—, —$(CH_2)_r$—O—$(CH_2)_s$—O—, —$(CH_2)_r$—CO—O—$(CH_2)_s$—O—, —$(CH_2)_r$—O—CO—$(CH_2)_s$—O—, —$(CH_2)_r$—$NR^1$—CO—$(CH_2)_s$—O—, —$(CH_2)_r$—$NR^1$—CO—O—$(CH_2)_s$—O—, —CO—O—$(CH_2)_r$—O—$(CH_2)_s$—O—, wherein $R^1$ is as defined above, r and s each represent an integer from 1 to 20, preferably from 1 to 12, and r+s≦21, preferably ≦15.

It is especially preferred that $S^1$ is selected from a single covalent bond, —$(CH_2)_r$—, —$(CH_2)_r$—O—, —$(CH_2)_r$—CO—O—, —$(CH_2)_r$—O—CO—, —$(CH_2)_r$—CO—NH—, —$(CH_2)_r$—NH—CO—, —CO—O—$(CH_2)_r$—, —CO—NH—$(CH_2)_r$—, —CO—O—$(CH_2)_r$—O—, —CO—NH—$(CH_2)_r$—O—, —$(CH_2)_r$—NH—CO—$(CH_2)_s$—, —$(CH_2)_r$—NH—CO—O—$(CH_2)_s$—, —$(CH_2)_r$—O—$(CH_2)_s$—O—, —$(CH_2)_r$—NH—CO—$(CH_2)_s$—O—, —$(CH_2)_r$—NHCO—O—$(CH_2)_s$—O—, —CO—O—$(CH_2)_r$—O—$(CH_2)_s$—O—, and —CO—$(CH_2)_r$—NH—CO—$(CH_2)_s$—O—, wherein r and s each represent an integer from 1 to 12 and r+s≦15.

Examples of preferred groups $S^1$ include 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 2-(methylenoxy)ethylene, 3-(methylenoxy)propylene, 4-(methylenoxy)butylene, 5-(methylenoxy)pentylene, 6-(methylenoxy)hexylene, 7-(methylenoxy)heptylene, 8-(methylenoxy)octylene, 9-(methylenoxy)nonylene, 10-(methylenoxy)decylene, 11-(methylenoxy)undecylene, 12-(methylenoxy)dodecylene, 2-(carbonyloxy)ethylene, 3-(carbonyloxy)propylene, 4-(carbonyloxy)butylene, 5-(carbonyloxy)pentylene, 6-(carbonyloxy)hexylene, 7-(carbonyloxy)heptylene, 8-(carbonyloxy)octylene, 9-(carbonyloxy)nonylene, 10-(carbonyloxy)decylene, 11-(carbonyloxy)undecylene, 12-(carbonyloxy)dodecylene, 2-(carbonylamino)ethylene, 3-(carbonylamino)propylene, 4-(carbonylamino)butylene, 5-(carbonylamino)pentylene, 6-(carbonylamino)hexylene, 7-(carbonylamino)heptylene, 8-(carbonylamino)octylene, 9-(carbonylamino)nonylene, 10-(carbonylamino)decylene, 11-(carbonylamino)undecylene, 12-(carbonylamino)dodecylene, 3-propyleneoxy, 3-propyleneoxycarbonyl, 2-ethylenoyloxy, 4-butyleneoxy, 4-butyleneoxycarbonyl, 3-propylenoyloxy, 5-pentyleneoxy, 5-pentyleneoxycarbonyl, 4-butylenoyloxy, 6-hexyleneoxy, 6-hexyleneoxycarbonyl, 5-pentylenoyloxy, 7-heptyleneoxy, 7-heptyleneoxycarbonyl, 6-hexylenoyloxy, 8-octyleneoxy, 8-octyleneoxycarbonyl, 7-heptylenoyloxy, 9-nonyleneoxy, 9-nonyleneoxycarbonyl, 8-octylenoyloxy, 10-decyleneoxy, 10-decyleneoxycarbonyl, 9-nonylenoyloxy, 11-undecyleneloxy, 11-undecyleneoxycarbonyl, 10-decylenoyloxy, 12-dodecyleneoxy, 12-dodecyleneoxycarbonyl, 11-undecylenoyloxy, 3-propyleneaminocarbonyl, 4-butyleneaminocarbonyl, 5-pentyleneaminocarbonyl, 6-hexyleneaminocarbonyl, 7-heptyleneaminocarbonyl, 8-octyleneaminocarbonyl, 9-nonyleneaminocarbonyl, 10-decyleneaminocarbonyl, 11-undecyleneaminocarbonyl, 12-dodecyleneaminocarbonyl, 2-ethylenecarbonylamino, 3-propylenecarbonylamino, 4-butylenecarbonylamino, 5-pentylenecarbonylamino, 6-hexylenecarbonylamino, 7-heptylenecarbonylamino, 8-octylenecarbonylamino, 9-nonylenecarbonylamino, 10-decylenecarbonylamino, 11-undecylenecarbonylamino, 2-(methylenoxy)ethanoyloxy, 3-(methylenoxy)propyloxy, 3-(methylenoxy)propyloxycarbonyl, 4-(methylenoxy)butyloxy, 4-(methylenoxy)butyloxycarbonyl, 3-(methylenoxy)propanoyloxy, 5-(methylenoxy)pentyloxy, 5-(methylenoxy)pentyloxycarbonyl, 4-(methylenoxy)butanoyloxy, 6-(methylenoxy)hexyloxy, 6-(methylenoxy)hexyloxycarbonyl, 5-(methylenoxy)pentanoyloxy, 7-(methylenoxy)heptyloxy, 7-(methylenoxy)heptyloxycarbonyl, 6-(methylenoxy)hexanoyloxy, 8-(methylenoxy)octyloxy, 8-(methylenoxy)octyloxycarbonyl, 7-(methylenoxy)heptanoyloxy, 9-(methylenoxy)nonyloxy, 9-(methylenoxy)nonyloxycarbonyl, 8-(methylenoxy)octanoyloxy, 10-(methylenoxy)decyloxy, 10-(methylenoxy)decyloxycarbonyl, 9-(methylenoxy)nonanoyloxy, 11-(methylenoxy)undecyloxy, 11-(methylenoxy)undecyloxycarbonyl, 10-(methylenoxy)decanoyloxy, 12-(methylenoxy)dodecyloxy, 12-(methylenoxy)dodecyloxycarbonyl, 11-(methylenoxy)undecanoyloxy, 3-(methylenoxy)propylaminocarbonyl, 4-(methylenoxy)butylaminocarbonyl, 5-(methylenoxy)pentylaminocarbonyl, 6-(methylenoxy)hexylaminocarbonyl, 7-(methylenoxy)heptylaminocarbonyl, 8-(methylenoxy)octylaminocarbonyl, 9-(methylenoxy)nonylaminocarbonyl, 10-(methylenoxy)decylaminocarbonyl, 11-(methylenoxy)undecylaminocarbonyl, 12-(methylenoxy)dodecylaminocarbonyl, 2-(methylenoxy)ethanoylamino, 3-(methylenoxy)propanoylamino, 4-(methylenoxy)butanoylamino, 5-(methylenoxy)pentanoylamino, 6-(methylenoxy)hexanoylamino, 7-(methylenoxy)heptanoylamino, 8-(methylenoxy)octanoylamino, 9-(methylenoxy)nonanoylamino, 10-(methylenoxy)decanoylamino, 11-(methylenoxy)undecanoylamino, 12-(methylenoxy)dodecylaminocarbonyl, 2-(carbonyloxy)ethanoyloxy, 3-(carbonyloxy)propyloxy, 3-(carbonyloxy)propyloxycarbonyl, 4-(carbonyloxy)butyloxy, 4-(carbonyloxy)butyloxycarbonyl, 3-(carbonyloxy)propanoyloxy, 5-(carbonyloxy)pentyloxy, 5-(carbonyloxy)pentyloxycarbonyl, 4-(carbonyloxy) butanoyloxy, 6-(carbonyloxy)hexyloxy, 6-(carbonyloxy)hexyloxycarbonyl, 5-(carbonyloxy)pentanoyloxy, 7-(carbonyloxy)heptyloxy, 7-(carbonyloxy)heptyloxycarbonyl, 6-(carbonyloxy)hexanoyloxy, 8-(carbonyloxy)octyloxy, 8-(carbonyloxy)octyloxycarbonyl, 7-(carbonyloxy)heptanoyloxy, 9-(carbonyloxy)nonyloxy, 9-(carbonyloxy)nonyloxycarbonyl, 8-(carbonyloxy)octanoyloxy, 10-(carbonyloxy)decyloxy, 10-(carbonyloxy)decyloxycarbonyl, 9-(carbonyloxy)nonanoyloxy, 11-(carbonyloxy)undecyloxy, 11-(carbonyloxy)undecyloxycarbonyl, 10-(carbonyloxy)decanoyloxy, 12-(carbonyloxy)dodecyloxy, 12-(carbonyloxy)dodecyloxycarbonyl, 11-(carbonyloxy)undecanoyloxy, 3-(carbonyloxy)propylaminocarbonyl, 4-(carbonyloxy)butylaminocarbonyl, 5-(carbonyloxy)pentylaminocarbonyl, 6-(carbonyloxy)hexylaminocarbonyl, 7-(carbonyloxy)heptylaminocarbonyl, 8-(carbonyloxy)octylaminocarbonyl, 9-(carbonyloxy)nonylaminocarbonyl, 10-(carbonyloxy)decylaminocarbonyl, 11-(carbonyloxy)undecylaminocarbonyl, 12-(carbonyloxy)dodecylaminocarbonyl, 2-(carbonyloxy)ethanoylamino, 3-(carbonyloxy)propanoylamino, 4-(carbonyloxy)butanoylamino, 5-(carbonyloxy)pentanoylamino, 6-(carbonyloxy)hexanoylamino, 7-(carbonyloxy)heptanoylamino, 8-(carbonyloxy)octanoylamino, 9-(carbonyloxy)nonanoylamino, 10-(carbonyloxy)decanoylamino, 11-(carbonyloxy)undecanoylamino, 12-(carbonyloxy)dodecylaminocarbonyl 6-(3-propyleneaminocarbonyloxy)hexylene, 6-(3-propyleneoxy)hexylene, 6-(3-propyleneoxy)hexyloxy, 6-(3-propyleneaminocarbonyloxy)hexyloxy, 6-(3-propyleneaminocarbonyl)hexyl, 6-(3-propyleneaminocarbonyl)hexyloxy, 2-(1-methyleneoxy)ethyloxycarbonyloxy, 3-(1-methyleneoxy)propyloxycarbonyloxy, 6-(1-methyleneoxy)hexyloxycarbonyloxy, 2-(1-methyleneoxycarbonyl)ethylene, 3-(1-methyleneoxycarbonyl)propyloxycarbonyloxy, 6-(1-methyleneoxycarbonyl)hexyloxycarbonyloxy, 6-(3-propyleneoxycarbonyloxy)hexylene, 6-(3-propyleneoxycarbonyl)hexylene, 2-(1-methyleneaminocarbonyl)ethylene, 3-(1-methyleneaminocarbonyl)propylene, 6-(1-methyleneaminocarbonyl)hexylene, 6-(3-propyleneaminocarbonyloxy)hexylene, 6-(3-propyleneaminocarbonyl)hexylene and the like.

It is preferred that the groups $Z^1$ and $Z^2$ are selected form a single covalent bond or a spacer unit such as a straight-chain or branched alkylene group, which is unsubstituted, mono or poly-substituted by fluoro atoms, having 1 to 8 carbon atoms, wherein one or more non-adjacent —$CH_2$— groups may independently be replaced by a group selected from —O—, —CO—, —CO—O—, —O—CO—, —$NR^1$—CO—, —CO—$NR^1$—, —CH=CH—, —C≡C—, and wherein $R^1$ represents a hydrogen atom or lower alkyl.

It is especially preferred that the groups $Z^1$ and $Z^2$ are selected form a single covalent bond or a spacer unit such a straight-chain or branched alkylene group having 1 to 4 carbon atoms, wherein one or two non-adjacent —$CH_2$— groups may independently be replaced by a group selected from —O—, —CO—, —CO—O—, —O—CO—.

It is preferred that n2=1 and n3=1.

It is especially preferred that n1=0 with n2=1 and n3=1.

If n1+n2+n3=0 then it is especially preferred that D is an organic group having a steroid skeleton.

It is preferred that the steroid skeleton is a 3-cholesteryl or a 3-cholestanyl residue.

By the terms —$(CH_2)_r$— and —$(CH_2)_s$— it should be understood to include straight-chain or branched alkylene groupings containing r or s carbon atoms respectively.

By the term "aromatic" it should be understood to include optionally substituted carbocylic and heterocyclic groups incorporating five, six or ten ring atoms, e.g. furan, phenyl, pyridine, pyrimidine, naphthalene, or tetraline units.

By the term "phenylene" it should be understood to include 1,2-, 1,3- or 1,4-phenylene, which is optionally substituted. It is preferred that the phenylene group is either a 1,3- or a 1,4-phenylene. 1,4-phenylene groups are especially preferred.

By the term "lower alkyl" it should be understood to include straight chain and branched hydrocarbon radicals having from 1 to 6 carbon atoms, preferably from 1 to 3 carbon atoms. Methyl, ethyl, propyl and isopropyl groups are especially preferred.

By the term "alicyclic" it should be understood to include non-aromatic carbocyclic or heterocyclic ring systems with 3 to 10 carbon atoms, e.g. cyclopropane, cyclobutane, cyclopentane, cyclopentene, cyclohexane, cyclohexene, cyclohexadiene and decaline.

By the term "cyclic, straight-chain or branched alkyl residue which is unsubstituted, mono-substituted by cyano or fluorine, chlorine, or poly-substituted by fluorine, chlorine, having 1 to 18 carbon atoms, wherein one or more non-adjacent —$CH_2$— groups may independently be replaced by a group B," it should be understood to include groups selected from the group comprising methyl, ethyl, propyl, isopropyl, butyl, isobutyl, sec-butyl, tert-butyl, pentyl, isopentyl, cyclopentyl, hexyl, cyclohexyl, heptyl, octyl, nonyl, decyl, undecyl, dodecyl, 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, cyclopentyloxy, hexyloxy, cyclohexyloxy, heptyloxy, octyloxy, nonyloxy, decyloxy, undecyloxy, dodecyloxy, 3-methylpentyloxy, allyloxy, but-3-enyloxy, pent-4-enyloxy, cylohexylmethoxy, cyclopentylmethoxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, cyclopentyloxycarbonyl, hexyloxycarbonyl, cyclohexyloxycarbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, cylohexylmethoxycarbonyl, cyclopentylmethoxycarbonyl, acetoxy, ethanoyloxy, propanoyloxy, isopropanoyloxy, butanoyloxy, isobutanoyloxy, sec-butanoyloxy, pentanoyloxy, isopentanoyloxy, cyclopentanoyloxy, hexanoyloxy, cyclohexanoyloxy, (4-propylcyclohexyl)methoxy, (4-propylcyclohexyl)carbonyloxy, (4-pentylbenzoyl)oxy, octanoyloxy, nonanoyloxy, decanoyloxy, undecanoyloxy, dodecanoyloxy, 3-methylpentanoyloxy, but-3-enyloxy, pent-4-enyloxy, acetyl, ethylcarbonyl, propylcarbonyl, isopropylcarbonyl, butylcarbonyl, isobutylcarbonyl, sec-butylcarbonyl, pentylcarbonyl, isopentylcarbonyl, cyclohexylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifluoromethyl, 2,2,2-trifluoroethyl, 1H, 1H-pentadecafluorooctyl, 1H,1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, perfluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

By the term "straight-chain or branched alkyl residue which is unsubstituted, mono-substituted by cyano or fluorine, chlorine, or poly-substituted by fluorine, chlorine, having 1 to 24 carbon atoms, wherein one or more non-adjacent —CH$_2$— groups may independently be replaced by a group B," it should be understood to include groups selected from the group comprising methyl, ethyl, propyl, isopropyl, butyl, isobutyl, sec-butyl, tert-butyl, pentyl, isopentyl, hexyl, heptyl, octyl, nonyl, decyl, undecyl, dodecyl, 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, hexyloxy, heptyloxy, octyloxy, nonyloxy, decyloxy, undecyloxy, dodecyloxy, 3-methylpentyloxy, allyloxy, but-3-enyloxy, pent-4-enyloxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, hexyloxycarbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, acetoxy, ethanoyloxy, propanoyloxy, isopropanoyloxy, butanoyloxy, isobutanoyloxy, sec-butanoyloxy, pentanoyloxy, isopentanoyloxy, hexanoyloxy, octanoyloxy, nonanoyloxy, decanoyloxy, undecanoyloxy, dodecanoyloxy, 3-methylpentanoyloxy, but-3-enyloxy, pent-4-enyloxy, acetyl, ethylcarbonyl, propylcarbonyl, isopropylcarbonyl, butylcarbonyl, isobutylcarbonyl, sec-butylcarbonyl, pentylcarbonyl, isopentylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifluoromethyl, 2,2,2-trifluoroethyl, 1H, 1H-pentadecafluorooctyl, 1H, 1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, perfluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

Further $A^1$ and $A^2$ each independently preferably represent a photoreactive group which can be photoisomerized and/or photodimerized on exposure to UV or laser light.

Preferably, the photoreactive groups are able to undergo photocyclization, in particular [2+2]-photocyclization.

Preferably, the photoreactive groups are sensitive to UV or laser light, in particular linearly polarized UV light.

Preferred photoreactive groups include cinnamates, benzylidenephthalimidines, benzylideneacetophones, diphenylacetylenes stilbazoles, uracyl, quinolinone, maleinimides, or cinnamylidene acetic acid derivatives, particularly preferred groups are cinnamates, coumarins, benzylideneacetophenones, or maleinimides.

Most preferred photoreactive groups are represented by general formulae IIIa and IIIb:

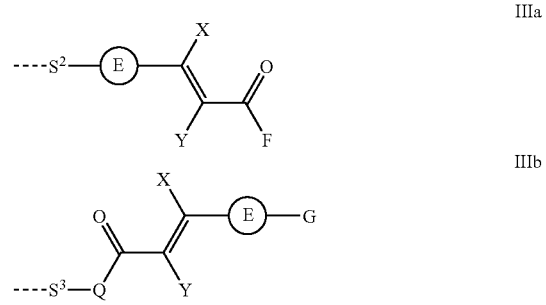

wherein

E represents pyrimidine-2,5-diyl, pyridine-2,5-diyl, 2,5-thiophenylene, 2,5-furanylene, 1,4- or 2,6-naphthylene, or phenylene, which is unsubstituted or mono- or poly-substituted by fluorine, chlorine or by a cyclic, straight-chain or branched alkyl residue which is unsubstituted or mono- or poly-substituted by fluorine, chlorine, having 1 to 18 carbon atoms, wherein one or more non-adjacent —CH$_2$— groups may independently be replaced by a group J, wherein J represents a group selected from —O—, —CO—, —CO—O—, —O—CO—, —NR$^1$—, —NR$^1$—CO—, —CO—NR$^1$—, —NR$^1$—CO—O—, —O—CO—NR$^1$—, —NR$^1$—CO—NR$^1$—, —CH═CH—, —C≡C—, —O—CO—O— and —Si(CH$_3$)$_2$—O—Si(CH$_3$)$_2$—, an aromatic or an alicyclic group, and wherein R$^1$ represents a hydrogen atom or lower alkyl;

F represents —OR$^2$, —NR$^3$R$^4$ or an oxygen atom, which defines together with the ring E a coumarin unit, wherein R$^2$, R$^3$ and R$^4$ are selected from hydrogen, a cyclic, straight-chain or branched alkyl residue which is unsubstituted, mono- or poly-substituted by fluorine, chlorine, having 1 to 24 carbon atoms, wherein one or more non-adjacent —CH$_2$— groups may independently be replaced by a group J, or R$^3$ and R$^4$ together form a C$_{5-8}$ alicyclic ring;

G represents a hydrogen atom, or a halogen atom, or a straight-chain or branched alkyl group which is unsubstituted, mono or poly-substituted by cyano, fluorine, chlorine, having 1 to 24 carbon atoms, wherein one or more —CH$_2$— groups may independently be replaced by a group J, with the proviso that oxygen atoms are not directly attached to each other;

S$^2$, S$^3$ each independently of the other represent a single bond or a spacer unit such as a straight-chain or branched alkylene group which is unsubstituted, mono or poly-substituted by fluorine, chlorine, or cyano, having 1 to 40 carbon atoms, wherein one or more —$CH_2$— groups may independently be replaced by a group J, with the proviso that oxygen atoms are not directly attached to each other;

Q represents an oxygen atom or —$NR^1$— wherein $R^1$ represents a hydrogen atom or lower alkyl;

X, Y each independently of the other represents hydrogen, fluorine, chlorine, cyano, alkyl optionally substituted by fluorine having 1 to 12 carbon atoms in which optionally one or more non-adjacent alkyl —$CH_2$— groups are replaced by —O—, —CO—O—, —O—CO— and/or —CH=CH—.

It is preferred that the group E is selected from pyrimidine-2,5-diyl, pyridine-2,5-diyl, 2,5-thiophenylene, 2,5-furanylene, 1,4- or 2,6-naphthylene and phenylene, which is unsubstituted or substituted by a cyclic, straight-chain or branched alkyl residue which is unsubstituted, mono- or poly-substituted by fluorine, chlorine having 1 to 12 carbon atoms in which optionally one or more non-adjacent alkyl —$CH_2$— groups are replaced by —O—, —CO—, —CO—O—, —O—CO—, —CH=CH— and —C≡C—.

It is especially preferred that the group E is selected from 2,5-furanylene, 1,4- or 2,6-naphthylene and phenylene, which is unsubstituted or substituted by a cyclic, straight-chain or branched alkyl residue having 1 to 12 carbon atoms in which optionally one or more non-adjacent alkyl —$CH_2$— groups are replaced by —O—, —CO—, —CO—O—, —O—CO—, —CH=CH— and —C≡C—.

It is preferred that the group F is selected from —$OR^2$ and —$NR^3R^4$, wherein $R^2$ and $R^3$ represent a cyclic, straight-chain or branched alkyl residue which is unsubstituted, mono- or poly-substituted by fluorine, chlorine, cyano, having 1 to 18 carbons atoms, wherein one or more non-adjacent alkyl —$CH_2$— groups may independently be replaced by —O— or —CH=CH—, wherein $R^4$ is selected from a hydrogen atom or a cyclic, straight-chain or branched alkyl residue which is unsubstituted, mono- or poly-substituted by fluorine, chlorine, cyano, having 1 to 18 carbons atoms, wherein one or more non-adjacent —$CH_2$— groups may independently be replaced by —O— or —CH=CH—, or $R^3$ and $R^4$ together to form a $C_{5-8}$ alicyclic ring.

It is especially preferred that F is selected from the group comprising —$OR^2$ or —$NHR^3$, wherein $R^2$ and $R^3$ represent a cyclic, straight-chain or branched alkyl residue which is unsubstituted, mono- or poly-substituted by fluorine atoms, having 1 to 18 carbon atoms, wherein one or more non-adjacent —$CH_2$— groups may independently be replaced by —O—.

It is preferred that the group G is a hydrogen atom, or fluorine atom, or chlorine atom, or a straight-chain or branched alkyl group which is unsubstituted, mono-substituted by cyano, fluorine or chlorine or poly-substituted by fluorine, chlorine, having 1 to 18 carbon atoms, wherein one or more —$CH_2$— groups may independently be replaced —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C— and —O—CO—O—, an aromatic or an alicyclic group, with the proviso that oxygen atoms are not directly attached to each other, and wherein $R^1$ represents a hydrogen atom or lower alkyl.

It is especially preferred that G is a hydrogen atom, or a straight-chain or branched alkyl group having 1 to 18 carbon atoms, wherein one or more non-adjacent —$CH_2$— groups may independently be replaced —O—, —CO—, —CO—O—, —O—CO—, —$NR^1$—, —$NR^1$—CO—, —CO—$NR^1$—, and —O—CO—O—, with the proviso that oxygen atoms are not directly attached to each other, and wherein $R^1$ represents a hydrogen atom or lower alkyl.

It is preferred that the group $S^2$ is selected from a single covalent bond, —CO—O—, —CO—$NR^1$—, —CO— and a straight-chain or branched alkylene group which is unsubstituted, mono or poly-substituted by fluorine, chlorine, or cyano, having 1 to 24 carbon atoms, wherein one or more —$CH_2$— groups may independently be replaced by a group J, with the proviso that oxygen atoms are not directly attached to each other, wherein $R^1$ represents a hydrogen atom or lower alkyl.

It is more preferred that $S^2$ is selected from a single covalent bond, —CO—O—, —CO—, —$(CH_2)_r$—, —$(CH_2)_r$—O—, —$(CH_2)_r$—CO—, —$(CH_2)_r$—CO—O—, —$(CH_2)_r$—O—CO—, —$(CH_2)_r$—CO—$NR^1$—, —CO—O—$(CH_2)_r$—O—, —$(CH_2)_r$—$NR^1$—CO—, —$(CH_2)_r$—$NR^1$—, —CO—O—$(CH_2)_r$—, —CO—$NR^1$—$(CH_2)_r$—, —CO—$NR^1$—$(CH_2)_r$—O—, —CO—$NR^1$—$(CH_2)_r$—$NR^1$—, —CO—$NR^1$—$(CH_2)_r$—O—CO—, —$(CH_2)_r$—O—$(CH_2)_s$—, —$(CH_2)_r$—CO—O—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$—CO—O—$(CH_2)_s$—, —$(CH_2)_r$—O—$(CH_2)_s$—O—, —$(CH_2)_r$—CO—O—$(CH_2)_s$—O—, —$(CH_2)_r$—O—CO—$(CH_2)_s$—O—, —$(CH_2)_r$—$NR^1$—CO—$(CH_2)_s$—O—, —$(CH_2)_r$—$NR^1$—CO—O—$(CH_2)_s$—O—, —CO—O—$(CH_2)_r$—O—$(CH_2)_s$— and —CO—O—$(CH_2)_r$—O—$(CH_2)_s$—O—, wherein $R^1$ is as defined above, r and s each represent an integer from 1 to 20, preferably from 1 to 12, and r+s≦21, preferably ≦15.

It is especially preferred that $S^2$ is selected from a single covalent bond, —$(CH_2)_r$—, —$(CH_2)_r$—O—, —$(CH_2)_r$—CO—O—, —$(CH_2)_r$—O—CO—, —$(CH_2)_r$—CO—NH—, —$(CH_2)_r$—NH—CO—, —CO—O—$(CH_2)_r$—, —CO—NH—$(CH_2)_r$—, —$(CH_2)_r$—NH—CO—$(CH_2)_s$—, —$(CH_2)_r$—NH—CO—O—$(CH_2)_s$—, —$(CH_2)_r$—O—$(CH_2)_s$—O—, —$(CH_2)_r$—NH—CO—$(CH_2)_s$—O—, —$(CH_2)_r$—NH—CO—O—$(CH_2)_s$—O—, —CO—O—$(CH_2)_r$—O—$(CH_2)_s$—O—, and —CO—$(CH_2)_r$—NH—CO—$(CH_2)_s$—O—, wherein r and s each represent an integer from 1 to 12 and r+s≦15.

Examples of preferred groups $S^2$ include 1,2-ethylen, 1,3-propylen, 1,4-butylen, 1,5-pentylen, 1,6-hexylen, 1,7-heptylen, 1,8-octylen, 1,9-nonylen, 1,10-decylen, 1,1,1-undecylen, 1,1,2-dodecylen, 3-methyl-1,4-butylen, 2-(methylenoxy)ethylen, 3-(methylenoxy)propylen, 4-methylenoxy)butylen, 5-(methylenoxy)pentylen, 6-(methylenoxy)hexylen, 7-(methylenoxy)heptylen, 8-(methylenoxy)octylen, 9-(methylenoxy)nonylen, 10-(methylenoxy)decylen, 11-(methylenoxy)undecylen, 12-(methylenoxy)dodecylen, 2-(carbonyloxy)ethylen, 3-(carbonyloxy)propylen, 4-(carbonyloxy)butylen, 5-(carbonyloxy)pentylen, 6-(carbonyloxy)hexylen, 7-(carbonyloxy)heptylen, 8-(carbonyloxy)octylen, 9-(carbonyloxy)nonylen, 10-(carbonyloxy)decylen, 11-(carbonyloxy)undecylen, 12-(carbonyloxy)dodecylen, 2-(carbonylamino)ethylen, 3-(carbonylamino)propylen, 4-(carbonylamino)butylen, 5-(carbonylamino)pentylen, 6-(carbonylamino)hexylen, 7-(carbonylamino)heptylen, 8-(carbonylamino)octylen, 9-(carbonylamino)nonylen, 10-(carbonylamino)decylen, 11-(carbonylamino)undecylen, 12-(carbonylamino)dodecylen, 3-propylenoxy, 3-propylenoxylcarbonyl, 2-ethylenoyloxy, 4-butylenoxy, 4-butylenoxycarbonyl, 3-propylenoyloxy, 5-pentylenoxy, 5-pentylenoxycarbonyl, 4-butylenoyloxy, 6-hexylenoxy, 6-hexylenoxycarbonyl, 5-pentylenoyloxy, 7-heptylenoxy, 7-heptylenoxycarbonyl, 6-hexylenoyloxy, 8-octylenoxy, 8-octylenoxycarbonyl, 7-heptylenoyloxy, 9-nonylenoxy, 9-nonylenoxycarbonyl, 8-octylenoyloxy, 10-decylenoxy, 10-decylenoxycarbonyl, 9-nonylenoyloxy, 11-undecylenoxy, 11-undecylenoxycarbonyl, 10-decylenoyloxy, 12-dodecylenoxy, 12-dodecylenoxycarbonyl, 11-undecylenoyloxy, 3-propylenaminocarbonyl, 4-butylenaminocarbonyl, 5-pentylenaminocarbonyl, 6-hexylenaminocarbonyl, 7-heptylenaminocarbonyl, 8-octylenaminocarbonyl, 9-nonylenaminocarbonyl, 10-decylenaminocarbonyl, 11-undecylenaminocarbonyl, 12-dodecylenaminocarbonyl, 2-ethylenoylamino, 3-propylenoylamino, 4-butylenoylamino, 5-pentylenoylamino, 6-hexylenoylamino, 7-heptylenoylamino, 8-octylenoylamino, 9-nonylenoylamino, 10-decylenoylamino, 11-undecylenoylamino, 2-(methylenoxy)ethanoyloxy, 3-(methylenoxy)propyloxy, 3-(methylenoxy)propyloxycarbonyl, 4-(methylenoxy)butyloxy, 4-(methylenoxy)butyloxycarbonyl, 3-(methylenoxy)propanoyloxy, 5-(methylenoxy)pentyloxy, 5-(methylenoxy)pentyloxycarbonyl, 4-(methylenoxy)butanoyloxy, 6-(methylenoxy)hexyloxy, 6-(methylenoxy)hexyloxycarbonyl, 5-(methylenoxy)pentanoyloxy, 7-(methylenoxy)heptyloxy, 7-(methylenoxy)heptyloxycarbonyl, 6-(methylenoxy)hexanoyloxy, 8-(methylenoxy)octyloxy, 8-(methylenoxy)octyloxycarbonyl, 7-(methylenoxy)heptanoyloxy, 9-(methylenoxy)nonyloxy, 9-(methylenoxy)nonyloxycarbonyl, 8-(methylenoxy)octanoyloxy, 10-(methylenoxy)decyloxy, 10-(methylenoxy)decyloxycarbonyl, 9-(methylenoxy)nonanoyloxy, 11-(methylenoxy)undecyloxy, 11-(methylenoxy)undecyloxycarbonyl, 10-(methylenoxy)decanoyloxy, 12-(methylenoxy)dodecyloxy, 12-(methylenoxy)dodecyloxycarbonyl, 11-(methylenoxy)undecanoyloxy, 3-(methylenoxy)propylaminocarbonyl, 4-(methylenoxy)butylaminocarbonyl, 5-(methylenoxy)pentylaminocarbonyl, 6-(methylenoxy)hexylaminocarbonyl, 7-(methylenoxy)heptylaminocarbonyl, 8-(methylenoxy)octylaminocarbonyl, 9-(methylenoxy)nonylaminocarbonyl, 10-(methylenoxy)decylaminocarbonyl, 11-(methylenoxy)undecylaminocarbonyl, 12-(methylenoxy)dodecylaminocarbonyl, 2-(methylenoxy)ethanoylamino, 3-(methylenoxy)propanoylamino, 4-(methylenoxy)butanoylamino, 5-(methylenoxy)pentanoylamino, 6-(methylenoxy)hexanoylamino, 7-(methylenoxy)heptanoylamino, 8-(methylenoxy)octanoylamino, 8-(methylenoxy)nonanoylamino, 10-(methylenoxy)decanoylamino, 11-(methylenoxy)undecanoylamino, 12-methylenoxy)dodecylaminoylamino, 2-(carbonyloxy)ethanoyloxy, 3-(carbonyloxy)propyloxy, 3-(carbonyloxy)propyloxycarbonyl, 4-(carbonyloxy)butyloxy, 4-(carbonyloxy)butyloxycarbonyl, 3-(carbonyloxy)propanoyloxy, 5-(carbonyloxy)pentyloxy, 5-(carbonyloxy)pentyloxycarbonyl, 4-(carbonyloxy)butanoyloxy, 6-(carbonyloxy)hexyloxy, 6-(carbonyloxy)hexyloxycarbonyl, 5-(carbonyloxy)pentanoyloxy, 7-(carbonyloxy)heptyloxy, 7-carbonyloxy)heptyloxycarbonyl, 6-(carbonyloxy)hexanoyloxy, 8-(carbonyloxy)octyloxy, 8-(carbonyloxy)octyloxycarbonyl, 7-(carbonyloxy)heptanoyloxy, 9-(carbonyloxy)nonyloxy, 9-(carbonyloxy)nonyloxycarbonyl, 8-(carbonyloxy)octanoyloxy, 10-(carbonyloxy)decyloxy, 10-(carbonyloxy)decyloxycarbonyl, 9-carbonyloxy)nonanoyloxy, 11-(carbonyloxy)undecyloxy, 11-(carbonyloxy)undecyloxycarbonyl, 10-(carbonyloxy)decanoyloxy, 12-(carbonyloxy)dodecyloxy, 12-(carbonyloxy)dodecyloxycarbonyl, 11-carbonyloxy)undecanoyloxy, 3-(carbonyloxy)propylaminocarbonyl, 4-(carbonyloxy)butylaminocarbonyl, 5-(carbonyloxy)pentylaminocarbonyl, 6-(carbonyloxy)hexylaminocarbonyl, 7-(carbonyloxy)heptylaminocarbonyl, 8-carbonyloxy)octylaminocarbonyl, 9-(carbonyloxy)nonylaminocarbonyl, 10-(carbonyloxy)decylaminocarbonyl, 11-(carbonyloxy)undecylaminocarbonyl, 12-(carbonyloxy)dodecylaminocarbonyl, 2-(carbonyloxy)ethanoylamino, 3-(carbonyloxy)propanoylamino, 4-(carbonyloxy)butanoylamino, 5-(carbonyloxy)pentanoylamino, 6-(carbonyloxy)hexanoylamino, 7-(carbonyloxy)heptanoylamino, 8-(carbonyloxy)octanoylamino, 9-(carbonyloxy)nonanoylamino, 10-(carbonyloxy)decanoylamino, 11-(carbonyloxy)undecanoylamino, 12-(carbonyloxy)dodecylaminocarbonyl, 6-(3-propylenaminocarbonyloxy)hexylen, 6-(3-propylenoxy)hexylen, 6-(3-propylenoxy)hexyloxy, 6-(3-propylenaminocarbonyloxy)hexyloxy, 6-(3-propylenaminocarbonyl)hexyl, 6-(3-propylenaminocarbonyl)hexyloxy, 2-(methylenoxy)ethyloxycarbonyloxy, 3-(methylenoxy)propyloxycarbonyloxy, 6-(methylenoxy)hexyloxycarbonyloxy, 2-(methylenoxycarbonyl)ethylen, 3-(methylenoxycarbonyl)propyloxycarbonyloxy, 6-(methylenoxycarbonyl)hexyloxycarbonyloxy, 6-(3-propylenoxycarbonyloxy)hexylen, 6-(3-propylenoxycarbonyl)hexylen, 2-(methylenaminocarbonyl)ethylen, 3-(methylenaminocarbonyl)propylen, 6-(methylenaminocarbonyl)hexylen, 6-(3-propylenaminocarbonyloxy)hexylen, 6-(3-propylenaminocarbonyl)hexylen, 4-{[6-(methylenoxy)hexyl]oxy}phenylen, 4-[6-(methylenoxy)hexyl]cyclohexylen, 3-methoxy-4-{[6-(methylenoxy)hexyl]oxy}phenylen, 4-{[6-(methylenoxy)hexyl]oxy}phenylcarbonyloxy, 4-[6-(methylenoxy)hexyl]cyclohexanoyloxy, 3-ethoxy-4-{[8-(methylenoxy)octyl-]oxy}phenylcarbonyloxy, 4-[3-(carbonyloxy)propyl]phenylen, 4-[6-(carbonyloxy)hexyl]phenylen, 4-[6-(carbonyloxy)hexyl]cyclohexylen, 3-methoxy-4-[6-(carbonyloxy)hexyl]phenylen, 4-[6-(carbonyloxy)hexyl]phenylcarbonyloxy, 4-[6-(carbonyloxy)hexyl]cyclohexanoyloxy, 3-ethoxy-4-[8-(carbonyloxy)octyl-]phenylcarbonyloxy, 2-{4-4-{2-(methylenoxy)ethyl}cyclohexyl]phenyl}ethoxy, 1-[4'-{[4-(methylenoxy)butyl]oxy}-1,1'biphenyl-4-yl]carbonyloxy, 1-{4-[4-{2-(methylenoxy)ethoxy}phenyl}methyloxy, 2-{4-[4-(2-carbonyloxyethyl) cyclohexyl]phenyl}ethoxy, 2-[4'-(4-carbonyloxybutyl)-1,1'biphenylen-4-yl]ethoxy, 6-(4-[4-(2-carbonyloxyethyl)phenyl]hexyloxy, 5-{[4'-[4-(methylenoxy)butoxy)]-1,1'-biphenyl-4-yl] oxy}pentanoyloxy and the like.

It is preferred that the group $S^3$ is selected from —CO—O—, —CO—NR$^1$—, —CO— and a straight-chain or branched alkylene group which is unsubstituted, mono or poly-substituted by fluorine, chlorine, or cyano, having 1 to 24 carbon atoms, wherein one or more —CH$_2$— groups may independently be replaced by a group J, with the proviso that oxygen atoms are not directly attached to each other, wherein R$^1$ represents a hydrogen atom or lower alkyl.

It is especially preferred that $S^3$ is selected from a single covalent bond, —(CH$_2$)$_r$—, —CO—(CH$_2$)$_r$—, —CO—O—(CH$_2$)$_r$—, —CO—NR$^1$—(CH$_2$)$_r$—, —(CH$_2$)$_r$—O—(CH$_2$)$_s$—, —(CH$_2$)$_r$—CO—O—(CH$_2$)$_s$—, —(CH$_2$)$_r$—O—CO—(CH$_2$)$_s$—, —(CH$_2$)$_r$—NR$^1$—CO—(CH$_2$)$_s$—, —(CH$_2$)$_r$—NR$^1$—CO—O—(CH$_2$)$_s$—, and —CO—O—(CH$_2$)$_r$—O—(CH$_2$)$_s$—, wherein R$^1$ is as defined herein above; r and s each represent an integer from 1 to 20; and r+s≦21. It is more preferred that r and s each represent an integer from 1 to 12. It is especially preferred that r+s≦15.

Examples of preferred groups $S^3$ include 1,2-ethylen, 1,3-propylen, 1,4-butylen, 1,5-pentylen, 1,6-hexylen, 1,7-heptylen, 1,8-octylen, 1,9-nonylen, 1,10-decylen, 1,11-undecylen, 1,12-dodecylen, 3-methyl-1,4-butylen, 2-(methylenoxy)ethylen, 3-(methylenoxy)propylen, 4-(methylenoxy)butylen, 5-methylenoxy)pentylen, 6-(methylenoxy)hexylen, 7-(methylenoxy)heptylen, 8-(methylenoxy)octylen, 9-(methylenoxy)nonylen, 10-(methylenoxy)decylen, 11-(methylenoxy)undecylen, 12-(methylenoxy)dodecylen, 2-(carbonyloxy)ethylen, 3-(carbonyloxy)propylen, 4-(carbonyloxy)butylen, 5-(carbonyloxy)pentylen, 6-(carbonyloxy)hexylen, 7-(carbonyloxy)heptylen, 8-(carbonyloxy)octylen, 9-(carbonyloxy)nonylen, 10-(carbonyloxy)decylen, 11-(carbonyloxy)undecylen, 12-(carbonyloxy)dodecylen, 2-(carbonylamino)ethylen, 3-(carbonylamino)propylen, 4-(carbonylamino)butylen, 5-carbonylamino)pentylen, 6-(carbonylamino)hexylen, 7-(carbonylamino)heptylen, 8-(carbonylamino)octylen, 9-(carbonylamino)nonylen, 10-(carbonylamino)decylen, 11-(carbonylamino)undecylen, 12-(carbonylamino)dodecylen, 6-(3-propylenaminocarbonyloxy)hexylen, 6-(3-propylenoxy)hexylen, 6-(3-propylenaminocarbonyl)hexyl, 2-(methylenoxycarbonyl)ethylen, 6-(3-propylenoxycarbonyloxy)hexylen, 6-(3-propylenoxycarbonyl)hexylen, 2-(methylenaminocarbonyl)ethylen, 3-(methylenaminocarbonyl)propylen, 6-(methylenaminocarbonyl)hexylen, 6-(3-propylenaminocarbonyloxy)hexylen, 6-(3-propylenaminocarbonyl)hexylen, 4-{[6-(methylenoxy)hexyl]oxy}phenylen, 4-[6-(methylenoxy)hexyl]cyclohexylen, 3-methoxy-4-{[6-(methylenoxy)hexyl]oxy}phenylen, 4-[3-(carbonyloxy)propyl]phenylen, 4-[6-(carbonyloxy)hexyl]phenylen, 4-[6-(carbonyloxy)hexyl]cyclohexylen, 3-methoxy-4-[6-(carbonyloxy)hexyl]phenylen and the like.

Preferred groups Q are oxygen atom or —NH—.

It is especially preferred that Q is an oxygen atom.

It is preferred that the groups X and Y represent hydrogen.

Preferred photoactive groups are groups of formula IIIa.

By the terms —$(CH_2)_r$— and —$(CH_2)_s$— it should be understood to include straight-chain or branched alkylene groupings containing r or s carbon atoms respectively.

By the term "aromatic" it should be understood to include optionally substituted carbocylic and heterocyclic groups incorporating five, six or ten ring atoms, e.g. furan, phenyl, pyridine, pyrimidine, naphthalene, or tetraline units.

By the term "phenylene" it should be understood to include 1,2-, 1,3- or 1,4-phenylene, which is optionally substituted. It is preferred that the phenylene group is either a 1,3- or a 1,4-phenylene. 1,4-phenylene groups are especially preferred.

By the term "lower alkyl" it should be understood to include straight chain and branched hydrocarbon radicals having from 1 to 6 carbon atoms, preferably from 1 to 3 carbon atoms. Methyl, ethyl, propyl and isopropyl groups are especially preferred.

By the term "alicyclic" it should be understood to include non-aromatic carbocyclic or heterocyclic ring systems with 3 to 10 carbon atoms, e.g. cyclopropane, cyclobutane, cyclopentane, cyclopentene, cyclohexane, cyclohexene, cyclohexadiene and decaline.

By the term "cyclic, straight-chain or branched alkyl residue which is unsubstituted, mono-substituted by cyano or fluorine, chlorine, or poly-substituted by fluorine, chlorine, having 1 to 18 carbon atoms, wherein one or more non-adjacent —$CH_2$— groups may independently be replaced by a group J," it should be understood to include groups selected from the group comprising methyl, ethyl, propyl, isopropyl, butyl, isobutyl, sec-butyl, tert-butyl, pentyl, isopentyl, cyclopentyl, hexyl, cyclohexyl, heptyl, octyl, nonyl, decyl, undecyl, dodecyl, 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, cyclopentyloxy, hexyloxy, cyclohexyloxy, heptyloxy, octyloxy, nonyloxy, decyloxy, undecyloxy, dodecyloxy, 3-methylpentyloxy, allyloxy, but-3-enyloxy, pent-4-enyloxy, cylohexylmethoxy, cyclopentylmethoxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, cyclopentyloxycarbonyl, hexyloxycarbonyl, cyclohexyloxycarbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, cylohexylmethoxycarbonyl, cyclopentylmethoxycarbonyl, acetoxy, ethanoyloxy, propanoyloxy, isopropanoyloxy, butanoyloxy, isobutanoyloxy, sec-butanoyloxy, pentanoyloxy, isopentanoyloxy, cyclopentanoyloxy, hexanoyloxy, cyclohexanoyloxy, (4-propylcyclohexyl)methoxy, (4-propylcyclohexyl)carbonyloxy, (4-pentylbenzoyl)oxy, octanoyloxy, nonanoyloxy, decanoyloxy, undecanoyloxy, dodecanoyloxy, 3-methylpentanoyloxy, but-3-enyloxy, pent-enyloxy, acetyl, ethylcarbonyl, propylcarbonyl, isopropylcarbonyl, butylcarbonyl, isobutylcarbonyl, sec-butylcarbonyl, pentylcarbonyl, isopentylcarbonyl, cyclohexylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifluoromethyl, 2,2,2-trifluoroethyl, 1H, 1H-pentadecafluorooctyl, 1H, 1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, perfluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

By the term "cyclic, straight-chain or branched alkyl residue which is unsubstituted, mono- or poly-substituted by fluorine, chlorine, having 1 to 24 carbon atoms, wherein one or more non-adjacent —$CH_2$— groups may independently be replaced by a group J," it should be understood to include groups selected from the group comprising methyl, ethyl, propyl, isopropyl, butyl, isobutyl, sec-butyl, tert-butyl, pentyl, isopentyl, hexyl, heptyl, octyl, nonyl, decyl, undecyl, dodecyl, 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, hexyloxy, heptyloxy, octyloxy, nonyloxy, decyloxy, undecyloxy, dodecyloxy, 3-methylpentyloxy, allyloxy, but-3-enyloxy, pent-4-enyloxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, hexyloxycarbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, acetoxy, ethanoyloxy, propanoyloxy, isopropanoyloxy, butanoyloxy, isobutanoyloxy, sec-butanoyloxy, pentanoyloxy, isopentanoyloxy, hexanoyloxy, octanoyloxy, nonanoyloxy, decanoyloxy, undecanoyloxy, dodecanoyloxy, 3-methylpentanoyloxy, but-3-enyloxy, pent-4-enyloxy, acetyl, ethylcarbonyl, propylcarbonyl, isopropylcarbonyl, butylcarbonyl, isobutylcarbonyl, sec-butylcarbonyl, pentylcarbonyl, isopentylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifluoromethyl, 2,2,2-trifluoroethyl, 1H, 1H-pentadecafluorooctyl, 1H,1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, Perfluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

By the term "straight-chain or branched alkylene group which is unsubstituted, mono or poly-substituted by fluorine, chlorine, or cyano, having 1 to 40 carbon atoms, wherein one or more —CH$_2$— groups may independently be replaced by a group J," it should be understood to include groups selected from the group comprising methyl, ethyl, propyl, isopropyl, butyl, isobutyl, sec-butyl, tert-butyl, pentyl, isopentyl, cyclopentyl, hexyl, cyclohexyl, heptyl, octyl, nonyl, decyl, undecyl, dodecyl, 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, cyclopentyloxy, hexyloxy, cyclohexyloxy, heptyloxy, octyloxy, nonyloxy, decyloxy, undecyloxy, dodecyloxy, 3-methylpentyloxy, allyloxy, but-3-enyloxy, pent-4-enyloxy, cylohexylmethoxy, cyclopentylmethoxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, cyclopentyloxycarbonyl, hexyloxycarbonyl, cyclohexyloxycarbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, cylohexylmethoxycarbonyl, cyclopentylmethoxycarbonyl, acetoxy, ethanoyloxy, propanoyloxy, isopropanoyloxy, butanoyloxy, isobutanoyloxy, sec-butanoyloxy, pentanoyloxy, isopentanoyloxy, cyclopentanoyloxy, hexanoyloxy, cyclohexanoyloxy, (4-propylcyclohexyl)methoxy, (4-propylcyclohexyl)carbonyloxy, (4-pentylbenzoyl)oxy, octanoyloxy, nonanoyloxy, decanoyloxy, undecanoyloxy, dodecanoyloxy, 3-methylpentanoyloxy, but-3-enyloxy, pent-4-enyloxy, acetyl, ethylcarbonyl, propylcarbonyl, isopropylcarbonyl, butylcarbonyl, isobutylcarbonyl, sec-butylcarbonyl, pentylcarbonyl, isopentylcarbonyl, cyclohexylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifluoromethyl, 2,2,2-trifluoroethyl, 1H, 1H-pentadecafluorooctyl, 1H, 1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, perfluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

A further object of the present invention is to provide a liquid crystal orientation material obtained by the reaction of a diamine compound represented by the general formula I.

A further object of the present invention is to provide a polymer from the class of polyamic acids, polyamic acid esters or polyimides obtained by the reaction of a diamine compound represented by the general formula I and optionally one or more additional diamines, with one or more tetracarboxylic acid anhydride of general formula IV:

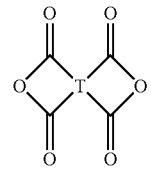

IV wherein T represents a tetravalent organic radical.

The tetravalent organic radical T is preferably derived from an aliphatic, alicyclic or aromatic tetracarboxylic acid dianhydride.

Preferred examples of alicyclic or aliphatic tetracarboxylic acid dianhydrides are
1,1,4,4-butanetetracarboxylic acid dianhydride,
ethylenemaleic acid dianhydride,
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
3,5,6-tricarboxynorbornylacetic acid dianhydride,
2,3,4,5-tetrahydrofurantetracarboxylic acid dianhydride,
rel-[1S,5R,6R]-3-oxabicyclo[3.2.1]octane-2,4-dione-6-spiro-3'-tetrahydrofuran-2',5'-dione),
4-(2,5-dioxotetrahydrofuran-3-yl)tetrahydronaphthalene-1,2-dicarboxylic acid dianhydride,
5-(2,5-dioxotetrahydrofuran-3-yl)-3-methyl-3-cyclohexene-1,2-dicarboxylic acid dianhydride,
bicyclo[2.2.2]oct-7-ene-2,3,5,6-tetracarboxylic acid dianhydride,
bicyclo[2.2.2]octane-2,3,5,6-tetracarboxylic acid dianhydride,
1,8-dimethylbicyclo[2.2.2]oct-7-ene-2,3,5,6-tetracarboxylic acid dianhydride and the like.

Preferred examples of aromatic tetracarboxylic acid dianhydrides are pyromellitic acid dianhydride,
3,3',4,4'-benzophenonetetracarboxylic acid dianhydride,
4,4'-oxydiphthalic acid dianhydride,
3,3',4,4'-diphenylsulfonetetracarboxylic acid dianhydride,
1,4,5,8-naphthalenetetracarboxylic acid dianhydride,
2,3,6,7-naphthalenetetracarboxylic acid dianhydride,
3,3',4,4'-dimethyldiphenylsilanetetracarboxylic acid dianhydride,
3,3',4,4'-tetraphenylsilanetetracarboxylic acid dianhydride,
1,2,3,4-furantetracarboxylic acid dianhydride,
4,4'-bis(3,4-dicarboxyphenoxy)diphenyl sulfide dianhydride,
4,4'-bis(3,4-dicarboxyphenoxy)diphenyl sulfone dianhydride,
4,4'-bis(3,4-dicarboxyphenoxy)diphenylpropane dianhydride,
3,3',4,4'-biphenyltetracarboxylic acid dianhydride,
ethylene glycol bis(trimellitic acid) dianhydride,
4,4'-(1,4-phenylene)bis(phthalic acid) dianhydride,
4,4'-(1,3-phenylene)bis(phthalic acid) dianhydride,
4,4'-(hexafluoroisopropylidene)iphthalic acid dianhydride,
4,4'-oxydi(1,4-phenylene)bis(phthalic acid) dianhydride,
4,4'-methylenedi(1,4-phenylene)bis(phthalic acid) dianhydride and the like.

More preferably, the tetracarboxylic acid dianhydrides used to form the tetravalent organic radical T are selected from
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride, 5-(2,5-dioxotetrahydrofuran-3-yl)-3-methyl-3-cyclohexene-1,2-dicarboxylic acid dianhydride, 4-(2,5-dioxotetrahydrofuran-3-yl)tetrahydronaphthalene-1,2-dicarboxylic acid dianhydride, 4,4'-(hexafluoroisopropylidene)diphthalic acid dianhydride and bicyclo[2.2.2]oct-7-ene-2,3,5,6-tetracarboxylic acid dianhydride.

A further object of the present invention is to provide a diamine compound represented by general formula I, which may be used alone or in combination with one or more diamine.

Preferred examples of additional diamines are ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'-diamino-p-xylene, (5-amino-2,2,4-trimethylcyclopentyl)methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)fluorene, 4,4'-methylenebis(2-chloroaniline), 4,4'-bis(4-aminophenoxy)biphenyl, 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene)bisaniline, 4,4'-(1,3-phenyleneisopropylidene)bisaniline, 2,2-bis[4-(4-aminophenoxy)phenyl]propane, 2,2-bis[3-(4-aminophenoxy)phenyl]hexafluoropropane, 2,2-bis[3-amino-4-methylphenyl]hexafluoropropane, 2,2-bis(4-aminophenyl)hexafluoropropane, 2,2'-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl, as well as diamines disclosed in U.S. Pat. No. 6,340,506, and PCT Patent Applications Publication Nos. WO 00/59966 and WO 01/53384, all of which are incorporated herein by reference.

When a diamine of the present invention is used alone, it is preferred that $A^1$ and $A^2$ each independently represent a photoreactive group that can be photoisomerized and/or photodimerized on exposure to UV or laser light.

Preferred polyamic acid, polyamic acid ester or polyimide are those which comprise as side-chains a photoreactive group that can be photoisomerized and/or photodimerized on exposure to UV or laser light. It is preferred that at least 75% of the repeating units include a side chain with a photoreactive group.

The diamines and the polymers of the invention may be prepared using methods that are known to a person skilled in the art and a next aspect of the invention provides a method of preparing compounds as defined above.

Polyamic acids and polyimides of the present invention may be prepared in accordance with known methods, such as those described in *Plast. Eng.* 36 (1996) (Polyimides, fundamentals and applications).

For example, the polycondensation reaction for the preparation of the polyamic acids is carried out in solution in a polar aprotic organic solvent, such as γ-butyrolactone, N,N-dimethylacetamide, N-methylpyrrolidone or N,N-dimethyl-formamide. In most cases equimolar amounts of the dianhydride and the diamine are used, i.e. one amino group per anhydride group. If it is desired to stabilize the molecular weight of the polymer, it is possible for that purpose to add an excess or a less-than-stoichiometric amount of one of the two components or to add a monofunctional compound in the form of a dicarboxylic acid monoanhydride or in the form of a monoamine. Examples of such monofunctional compounds are maleic acid anhydride, phthalic acid anhydride, aniline and so on. The reaction is carried out preferably at a temperature of less than 100° C.

The cyclisation of the polyamic acids to form the polyimides can be carried out by heating, i.e. by condensation with removal of water or by other imidisation reactions with reagents. When carried out purely thermally, the imidisation of the polyamic acids is not always complete, i.e. the resulting polyimides may still contain proportions of polyamic acid. The imidisation reactions are generally carried out at a temperature of from 60 to 250° C., but preferably at less than 200° C. In order to achieve imidisation at rather lower temperatures, there are additionally mixed into the reaction mixture reagents that facilitate the removal of water. Such reagents are, for example, mixtures consisting of acid anhydrides, such as acetic acid anhydride, propionic acid anhydride, phthalic acid anhydride, trifluoroacetic acid anhydride, and tertiary amines, such as triethylamine, trimethylamine, tributylamine, pyridine, N,N-dimethylaniline, lutidine, collidine etc. The amount of reagents used in that case is preferably at least two equivalents of amine and four equivalents of acid anhydride per equivalent of polyamic acid to be condensed.

The imidisation reaction can be carried out before or alternatively only after application to a support.

The polyamic acids and the polyimides of the present invention have an intrinsic viscosity preferably in the range of 0.05 to 10 dL/g, more preferably 0.05 to 5 dL/g. Herein, the intrinsic viscosity ($\eta_{inh}$=ln $\eta_{rel}$/C) is determined by measuring a solution containing a polymer in a concentration of 0.5 g/100 ml for its viscosity at 30° C. using N-methyl-2-pyrrolidone as solvent.

The polyamic acid chains or polyimide chains of the present invention preferably contain from 2 to 2000 repeating units, especially from 3 to 200.

Additives such as silane-containing compounds and epoxy-containing cross-linking agents may be added to the polymers of the invention in order to improve the adhesion of the polymer to a substrate. Suitable silane-containing compounds are described in *Plast. Eng.* 36 (1996) (Polyimides, fundamentals and applications). Suitable epoxy-containing crosslinking agents include 4,4'-methylene-bis-(N,N-diglycidylaniline), trimethylolpropane triglycidyl ether, benzene-1,2,4,5-tetracarboxylic acid 1,2:4,5-N,N'-diglycidyldiimide, polyethylene glycol diglycidyl ether, N,N-diglycidylcyclohexylamine and the like.

Additional additives such as a photosensitizer, a photoradical generator and/or a cationic photoinitiator may also be added to the polymers of the invention. Suitable photoactive additives include 2,2-dimethoxyphenylethanone, a mixture of diphenylmethanone and N,N-dimethylbenzenamine or ethyl 4-(dimethylamino)benzoate, xanthone, thioxanthone, Irgacure™ 184, 369, 500, 651 and 907 (Ciba), Michler's ketone, triaryl sulfonium salt and the like.

The polymers according to the invention may be used in form of polymer layers alone or in combination with other polymers, oligomers, monomers, photoactive polymers, photoactive oligomers and/or photoactive monomers, depending upon the application to which the polymer layer is to be put. It will therefore be appreciated that by varying the composition of the polymer layer it is possible to control properties such as an induced pretilt angle, good surface welting, high voltage holding ratio, a specific anchoring energy etc.

Polymer layers may be readily prepared from the polymers of the present invention and a further aspect of the invention provides a polymer layer comprising a polymer according to the present invention in a crosslinked form.

The polymer layer is preferably prepared by applying one or more polymers according to the invention to a support and, after any imidisation step which may be necessary, crosslinking the polymer or polymer mixture by irradiation with linearly polarized light. It is possible to vary the direction of orientation and the tilt angle within the polymer layer by controlling the direction of irradiation of the linearly polarized light. It will be appreciated that by selectively irradiating specific regions of the polymer layer it is possible to align very specific regions of the layer and provide layers with a defined angle of tilt. This orientation and tilt is retained in the polymer layer by the process of crosslinking.

It will be appreciated that the polymer layers of the present invention can also be used as orientation layers for liquid crystals and a preferred embodiment of the invention provides an orientation layer comprising one or more polymers according to the invention in a crosslinked form. Such orientation layers can be used in the manufacture of optical constructional elements, preferably in the production of hybrid layer elements.

The orientation layers are suitably prepared from a solution of the polymer material. The polymer solution is applied to a support optionally coated with an electrode (for example a glass plate coated with indium-tin oxide (ITO)) so that homogeneous layers of 0.05 to 50 μm thickness are produced. In this process different coating techniques like spincoating, miniscuscoating, wirecoating, slotcoating, offsetprinting, flexoprinting, gravurprinting may be used. Then, or optionally after prior imidisation, the regions to be oriented can be irradiated, for example, with a high-pressure mercury vapour lamp, a xenon lamp or a pulsed UV laser, using a polarizer and optionally a mask for creating images of structures. The irradiation time is dependent upon the output of the individual lamps and can vary from a few seconds to several hours. The dimerisation can also be carried out, however, by irradiation of the homogeneous layer using filters that, for example, allow only the radiation suitable for the crosslinking reaction to pass through.

It will be appreciated that the polymer layers of the invention may be used in the production of optical or electro-optical devices as well as unstructured and structured optical elements and multi-layer systems.

A further embodiment of the invention provides an optical or electro-optical device comprising one or more polymers according to the first aspect of the invention in crosslinked form. The electro-optical devices may comprise more than one layer. The or each of the layers may contain one or more regions of different spatial orientation.

The diamines and polymers in accordance with the invention are illustrated in more detail by the following examples.

SYNTHESIS EXAMPLE 1

Bis [6-({4-[(1E)-3-methoxy-3-oxoprop-1-enyl]benzoyl}oxy)hexyl]2,2-bis(amino-benzyl)malonate was prepared in accordance with the following procedure.

Preparation of bis [6-({4-[(1E)-3-methoxy-3-oxo-prop-1-enyl]benzoyl}oxy)hexyl]malonate

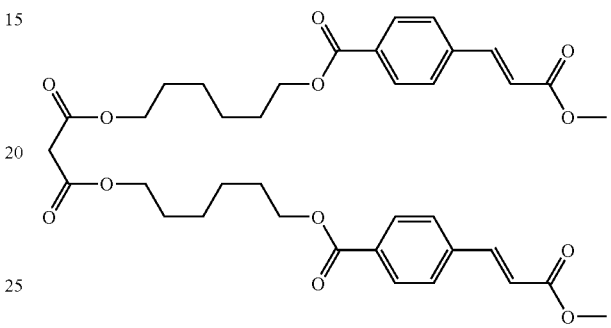

5.00 g (16.32 mmol) 6-hydroxyhexyl 4-[(1E)-3-methoxy-3-oxoprop-1-enyl]benzoate, 1.02 g (9.80 mmol) malonic acid ester and 0.50 g (4.09 mmol) 4-dimethylaminopyridine were dissolved in 150 ml of dichloromethane. A suspension of 3.75 g (19.56 mmol) N-(3-dimethylaminopropyl)-N'-ethylcarbodiimide hydrochloride and 100 ml dichloromethane were added dropwise in the course of 40 minutes. After 22 hours at room temperature the reaction mixture was partitioned between dichloromethane and water; the organic phase was washed repeatedly with water, dried over sodium sulfate, filtered and concentrated by rotary evaporation. Chromatography of the residue on 110 g silica gel using toluene:ethyl acetate (9:1) then (1:1) as eluant yielded 2.14 g (39%) bis [6-({4-[(1E)-3-methoxy-3-oxoprop-1-enyl]benzoyl}oxy)hexyl]malonate as color-less crystals.

Preparation of bis [6-({4-[(1E)-3-methoxy-3-oxo-prop-1-enyl]benzoyl}oxy)hexyl]2,2 bis(4-nitrobenzyl)malonate

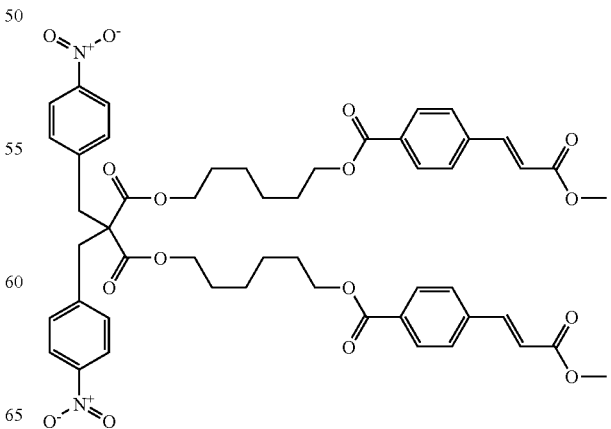

2.12 g (3.11 mmol) bis [6-({4-[(1E)-3-methoxy-3-oxoprop-1-enyl]benzoyl}oxy)-hexyl]malonate and 1.34 g (6.22 mmol) 4-nitrobenzylbromide were dissolved in 25 ml dioxane. A suspension of 136 mg (3.12 mmol) sodium hydride 55% dispersion in mineral oil and 4 ml dioxane were added in 1 hour. After 1 hour, another suspension of 136 mg (3.12 mmol) sodium hydride 55% dispersion in mineral oil and 4 ml dioxane were added. After 18.5 hours at room temperature, the reaction mixture was concentrated by evaporation. The residue was partitioned between water and ethyl acetate; the organic phase was washed repeatedly with water, dried over sodium sulfate, filtered and concentrated by rotary evaporation. Chromatography of the residue on 50 g silica gel using toluene:ethyl acetate 95:5 as eluant and recrystallisation form ethyl acetate:hexane (3:5) yielded 1.32 g (45%) bis [6-({4-[(1E)-3-methoxy-3-oxoprop-1-enyl]benzoyl}oxy)hexyl]2,2 bis(4-nitrobenzyl) malonate as white powder.

Preparation of bis [6-({4-[(1E)-3-methoxy-3-oxoprop-1-enyl]benzoyl}oxy)hexyl-]2,2 bis(4-aminobenzyl) malonate

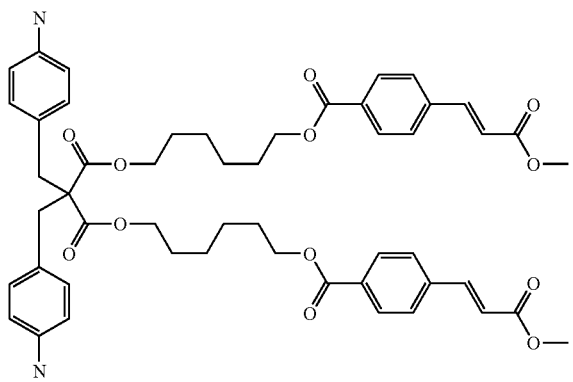

1.30 g (1.36 mmol) bis [6-({4-[(1E)-3-methoxy-3-oxoprop-1-enyl]benzoyl}oxy)-hexyl]2,2 bis(4-nitrobenzyl) malonate were dissolved in a mixture of 25 ml N,N-dimethylformamide and 2.8 ml water. 2.21 g (8.18 mmol) ferric chloride hexahydrate and 0.716 g (10.95 mmol) Zinc powder were added, the temperature rise to 40° C. The mixture was allowed to react for 1 hours. The black reaction mixture was then partitioned between ethyl acetate and water and filtered. The organic phase was washed repeatedly with water, dried over sodium sulfate, filtered and concentrated by rotary evaporation. A first chromatography on 50 g silica gel using tert-butyl methyl ether as eluant and a second chromatography on 25 g silica gel using toluene:ethyl acetate (9:1) then (4:1) as eluant yielded 0.78 g (64%) of bis [6-({4-[(1E)-3-methoxy-3-oxoprop-1-enyl]benzoyl}oxy)hexyl]2,2 bis(4-aminobenzyl) malonate as a yellow powder.

The following diamines were synthesized in a analogous manner:

bis [8-({4-[(1E)-3-methoxy-3-oxoprop-1-enyl]benzoyl}oxy)octyl]2,2 bis(4-aminobenzyl) malonate, bis [6-({4-[(1E)-3-ethoxy-3-oxoprop-1-enyl]benzoyl}oxy)hexyl]2,2 bis(4-aminobenzyl) malonate, bis [6-{4-[(1E)-3-methoxy-3-oxoprop-1-enyl]phenoxy}hexyl]2,2 bis(4-aminobenzyl) malonate, bis [11-{4-[(1E)-3-methoxy-3-oxoprop-1-enyl]phenoxy}undecyl]2,2 bis(4-aminobenzyl) malonate, bis [11-{4-[(1E)-3-hexyloxy-3-oxoprop-1-enyl]phenoxy}undecyl]2,2 bis(4-aminobenzyl) malonate, and bis [6-({4-[(1E)-3-cyclohexyloxy-3-oxoprop-1-enyl]benzoyl}oxy)hexyl]2,2 bis(4-aminobenzyl) malonate.

SYNTHESIS EXAMPLE 2

[6-({4-[(1E)-3-methoxy-3-oxoprop-1-enyl]benzoyl}oxy)hexyl]2-(4-nitrobenzyl)-3-(4-nitrophenyl) propanoate was prepared in accordance with the following procedure.

Preparation of 2,2-dimethyl-5,5-bis(4-nitrobenzyl)-1,3-dioxane-4,6-dione

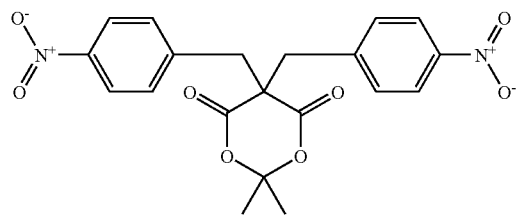

15.0 g (69.4 mmol) of 4-nitrobenzylbromide and 5.00 g (34.7 mmol) of Meldrum's acid were dissolved in 100 ml 2-butanone. 4.40 g (104.1 mmol) potassium carbonate were added, the resulting suspension was heated to 50° C. and allowed to react for 2.5 hours. After cooling to room temperature, 100 ml water were added. The product was collected by filtration and washed with a lot of water. 12.3 g (85%) of 2,2-dimethyl-5,5-bis(4-nitrobenzyl)-1,3-dioxane-4,6-dione as yellowish powder was used without further purification.

Preparation of 2,2-bis(4-nitrobenzyl)malonic acid

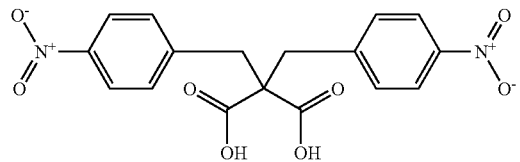

2.185 g (52.07 mmol) of lithium hydroxide were added to a suspension of 10.79 g (26.04 mmol) of 2,2-dimethyl-5,5-bis(4-nitrobenzyl)-1,3-dioxane-4,6-dione and 110 ml mixture of tetrahydrofuran:water 9:1. The mixture was subsequently allowed to react for 21.5 hours at 25° C., added to 500 ml water and acidified to pH=1 with 20 ml hydrochloric acid 3N. The mixture was partitioned between water and ethyl acetate; the organic phase was washed repeatedly with water, dried over sodium sulfate, filtered and concentrated by rotary evaporation. The residue 9.54 g (98%) of 2,2-bis(4-nitrobenzyl)malonic acid as white powder was used without further purification.

Preparation of 6-chlorohexyl 2-(4-nitrobenzyl)-3-(4-nitrophenyl) propanoate

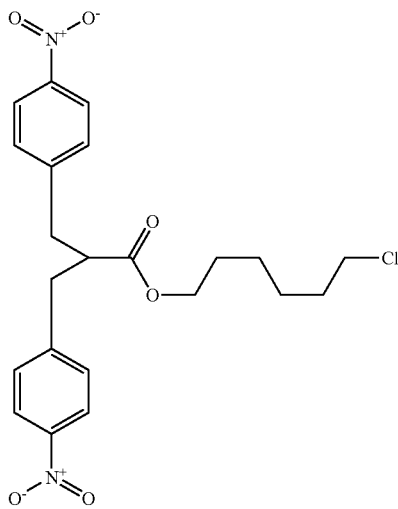

1.00 g (2.67 mmol) of 2,2-bis(4-nitrobenzyl)malonic acid and 1.42 ml (10.7 mmol) 6-chlorohexanol were suspended in 5.0 ml toluene. 1.0 ml sulphuric acid are added. The reaction mixture was subsequently allowed to react for 21.5 hours at refluxing temperature. The reaction mixture was partitioned between water and ethyl acetate; the organic phase was washed repeatedly with water, dried over magnesium sulfate, filtered and concentrated by rotary evaporation. Chromatography of the residue on 150 g silica gel using toluene:ethyl acetate 19:1 as eluant yielded 0.94 g (78%) 6-chlorohexyl 2-(4-nitrobenzyl)-3-(4-nitrophenyl) propanoate as yellow oil.

Preparation of 6-({4-[(1E)-3-methoxy-3-oxoprop-1-enyl]benzoyl}yloxy)hexyl 2-(4-nitrobenzyl)-3-(4-nitrophenyl) propanoate

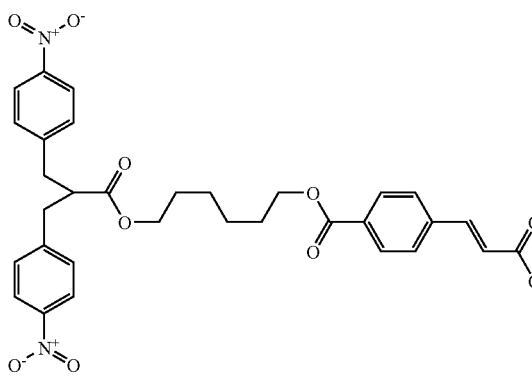

1.00 g (4.85 mmol) methyl (E)-4-carboxyl cinnamate were dissolved in 10 ml dimethylformamide. 0.73 ml (4.88 mmol) 1,8-diazabicyclo[5.4.0]undec-7-ene(1,5-5) (DBU) were added dropwise in the course of 3 minutes. The reaction temperature rise to 30° C., subsequently a mixture of 1.98 g (4.41 mmol) 6-chlorohexyl 2-(4-nitrobenzyl)-3-(4-nitrophenyl) propanoate and 4 ml dimethylformamide were added in one portion. The mixture was then heated at 80° C. for 22 hours. The reaction mixture was cooled and then partitioned between ethyl acetate and a saturated sodium bicarbonate solution; the organic phase was washed repeatedly with water, dried over sodium sulfate, filtered and concentrated by rotary evaporation. Chromatography of the residue on 100 g silica gel using toluene:ethyl acetate 9:1 as eluant yielded 2.80 g (98%) 6-({4-[(1E)-3-methoxy-3-oxoprop-1-enyl]benzoyl}oxy)hexyl 2-(4-nitrobenzyl)-3-(4-nitrophenyl) propanoate as yellow oil.

Preparation of 6-({4-[(1E)-3-methoxy-3-oxoprop-1-enyl]benzoyloxy}hexyl 2-(4-aminobenzyl)-3-(4-aminophenyl) propanoate

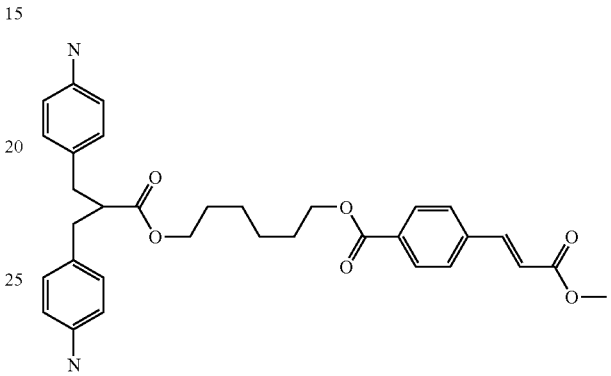

Preparation can be carried out analogously to Example 1 using 2.84 g (4.59 mmol) 6-({4-[(1E)-3-methoxy-3-oxoprop-1-enyl]benzoyl}oxy)hexyl 2-(4-nitrobenzyl)-3-(4-nitrophenyl) propanoate, 7.44 g (27.52 mmol) Ferric chloride hexahydrate and 3.00 g (45.89 mmol) Zinc powder yielded 1.93 g (72%) 6-({4-[(1E)-3-methoxy-3-oxoprop-1-enyl] benzoyl}oxy)hexyl 2-(4-aminobenzyl)-3-(4-aminophenyl) propanoate as yellow powder.

SYNTHESIS EXAMPLE 3

Cholest-5-en-3-yl 2-(4-aminobenzyl)-3-(4-aminophenyl) propanoate was prepared in accordance with the following procedure.

Preparation of cholest-5-en-3-yl 2-(4-nitrobenzyl)-3-(4-nitrophenyl)propanoate

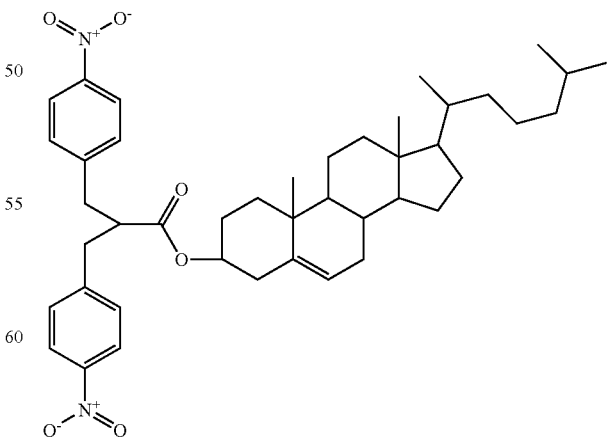

2.00 g (5.34 mmol) of 2,2-bis(4-nitrobenzyl)malonic acid and 2.07 g (5.35 mmol) 5-cholesten-3β-ol and 65 mg (0.53 mmol) 4-dimethylaminopyridine in 40 ml of dichloromethane were cooled to 0° C. and 1.16 g (5.62 mmol) N,N'-dicyclohexylcarbodiimde were added. The mixture was subsequently allowed to react for 2 hours at 0° C. and 19 hours at 25° C., filtered and concentrated by rotary evaporation. Chromatography of the residue on 50 g silica gel using toluene as eluant and recrystallisation form ethyl acetate yielded 3.09 g (83%) Cholest-5-en-3-yl 2-(4-nitrobenzyl)-3-(4-nitrophenyl)propanoate as a white powder.

Preparation of Cholest-5-en-3-yl 2-(4-aminobenzyl)-3-(4-aminophenyl)-propanoate

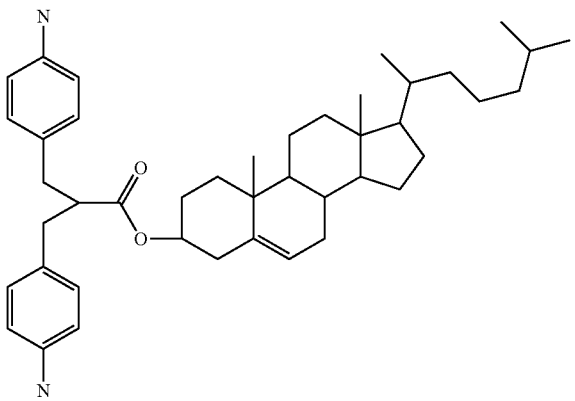

2.62 g (3.75 mmol) Cholest-5-en-3-yl 2-(4-nitrobenzyl)-3-(4-nitrophenyl)-propanoate and 0.79 g (14.77 mmol) ammonium chloride were suspended in 90 ml of a mixture consisting of methanol:water 9:1. 4.90 g (74.96 mmol) zinc powder was then added in 10 minutes. The reaction mixture was then allowed to react at 45° C. for 6 hours and partitioned between dichloromethane and water; the organic phase was washed repeatedly with water, dried over sodium sulfate, filtered and concentrated by rotary evaporation. First chromatography of the residue on 50 g silica gel using toluene:ethyl acetate 1:1 as eluant and second chromatography on 50 g silica gel using tert.butyl methylether as eluant yielded 1.66 g Cholest-5-en-3-yl 2-(4-aminobenzyl)-3-(4-aminophenyl)-propanoate as white powder.

SYNTHESIS EXAMPLE 4

2,2-bis(4-nitrobenzyl)-1,3 di(6-bromohexanoyl)propanediol was prepared in accordance with the following procedure.

Preparation of 2,2-bis(4-nitrobenzyl)-1,3-propandiol

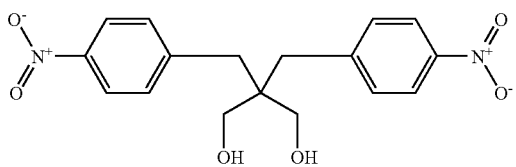

4.00 g (10.69 mmol) 2,2-bis(4-nitrobenzyl)malonic acid were dissolved in 40 ml tetrahydrofuran and added dropwise in a the course of 2 hours to 64.1 ml (64.1 mmol) of a borane-tetrahydrofuran complex 1.0 M solution in tetrahydrofuran. After 19 hours at 25° C., 50 ml water were carefully added. The reaction mixture was then partitioned between ethyl acetate and water; the organic phase was washed repeatedly with water, dried over sodium sulfate, filtered and concentrated by rotary evaporation. The residue, 3.77 g (97%) of a white powder was used without further purification.

Preparation of 2,2-bis(4-nitrobenzyl)-1,3 di(6-bromohexanoyl)propanediol

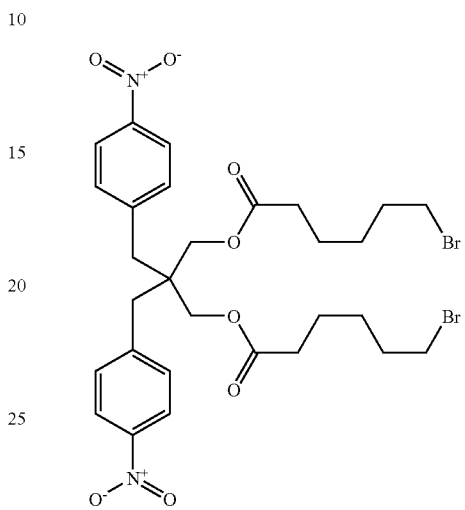

3.77 g (10.88 mmol) of 2,2-bis(4-nitrobenzyl)-1,3-propandiol, 4.25 g (21.79 mmol) 6-bromohexanoic acid and 32 mg (2.6 mmol) 4-dimethylaminopyridine in 175 ml of dichloromethane were cooled to ° C. and 4.81 g (23.31 mmol) N,N'-dicyclohexylcarbodiimde were added. The mixture was subsequently allowed to react for 2 hours at 0° C. and 19 hours at 25° C., filtered and concentrated by rotary evaporation. Chromatography of the residue on 100 g silica gel using toluene:ethyl acetate (95:5) as eluant yielded 6.39 g (96%) of 2,2-bis(4-nitrobenzyl)-1,3 di(6-bromohexanoyl)propanediol as yellowish oil.

Preparation of 2,2-bis(4-nitrobenzyl)-1,3 di(6-{4-[(1E)-3-methoxy-3-oxoprop-1-enyl]phenoxy}hexanoyl)propanediol

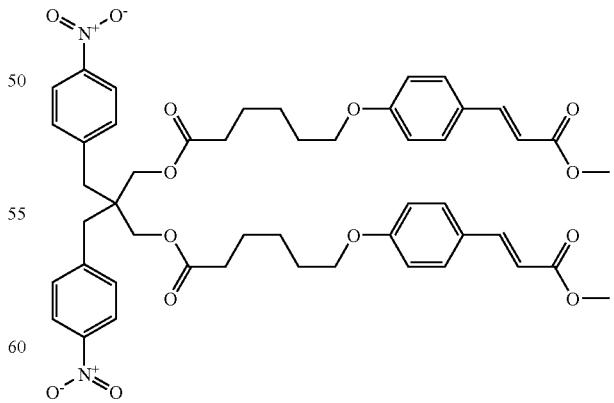

3.14 g (4.48 mmol) 2,2-bis(4-nitrobenzyl)-1,3 di(6-bromohexanoyl)propanediol and 1.60 g (8.98 mmol) methyl 4-hydroxycinnamate were dissolved in 24 ml 1-methyl-2-pyrrolidon. 2.45 g (17.73 mmol) potassium carbonate were added. The reaction suspension was then heated at 80° C. for 4 hours. The reaction mixture was partitioned between ethyl acetate and water. The organic phase was washed repeatedly with water, dried over sodium sulfate, filtered and concentrated by rotary evaporation. Chromatography of the residue yielded 3.72 g (88%) 2,2-bis(4-nitrobenzyl)-1,3 di(6-{4-[(1E)-3-methoxy-3-oxoprop-1-enyl]phenoxy}hexanoyl) propanediol as yellowish powder.

Preparation of 2,2-bis(4-aminobenzyl)-1,3 di(6-{4-[(1E)-3-methoxy-3-oxoprop-1-enyl] phenoxy}hexanoyl)propanediol

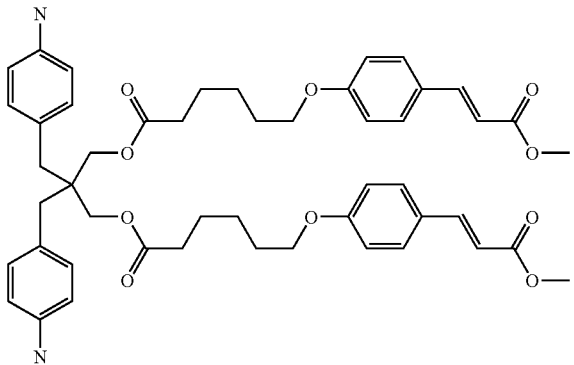

Preparation can be carried out analogously to Example 1 using 3.87 g (4.069 mmol) 2,2-bis(4-nitrobenzyl)-1,3 di(6-{4-[(1E)-3-methoxy-3-oxoprop-1-enyl]phenoxy}hexanoyl) propanediol, 6.59 g (24.380 mmol) ferric chloride hexahydrate and 2.66 g (40.69 mmol) Zinc powder yielded 2.91 g (80%) 6-({4-[(1E)-3-methoxy-3-oxoprop-1-enyl] benzoyl}oxy)hexyl 2-(4-aminobenzyl)-3-(4-amino-phenyl) propanoate as yellow powder.

The following diamines can be synthesized in a analogous manner:

2,2-bis(4-aminobenzyl)-1,3 di(6-{4-[(1E)-3-ethoxy-3-oxo-prop-1-enyl]phenoxy}hexanoyl) propanediol,
2,2-bis(4-aminobenzyl)-1,3 di(11-{4-[(1E)-3-ethoxy-3-oxo-prop-1-enyl]phenoxy}undecanoyl) propanediol,
2,2-bis(3-aminobenzyl)-1,3 di(6-{4-[(1E)-3-methoxy-3-oxoprop-1-enyl]phenoxy}hexanoyl) propanediol, and
2,2-bis(2-aminobenzyl)-1,3 di(6-{4-[(1E)-3-methoxy-3-oxoprop-1-enyl]phenoxy}hexanoyl) propanediol.

SYNTHESIS EXAMPLE 5

Bis [8-({(2E)-3-[3-methoxy-4-(pentyloxy)phenyl)prop-2-enoyl}oxy)octyl]2,2-bis(aminobenzyl)malonate was prepared in accordance with the following procedure.

Preparation of (2E)-3-[3-methoxy-4-(pentyloxy) phenyl]prop-2-enoic acid

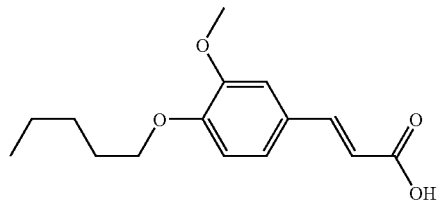

5.00 g (32.86 mmol) Vanilin, 4.88 ml (39.48 mmol) n-pentylbromide and 13.62 g (98.59 mmol) potassium carbonate were dissolved in 50 ml 1-methyl-2-pyrrolidone. The reaction suspension was allowed to react for 6 hours at 25° C.

Subsequently 8.55 ml (59.34 mmol) trimethylphosphonoacetate were added. The mixture was allowed to react for 18 hours at 25° C. Then 20 ml of a sodium hydroxide solution 28% in water were added. The reaction mixture was allowed to react for 1.5 hour at 70° C. After cooling, the mixture was acidified to pH=1 with hydrochloric acid 37 wt. %. The product was filtered off, washed with water and dried at 40° C. under vacuum to give 7.36 g (84.7%) (2E)-3-[3-methoxy-4-(pentyloxy)phenyl]prop-2-enoic acid as beige crystals.

Preparation of 6-hydroxyhexyl (2E)-3-[3-methoxy-4-(pentyloxy)phenyl]prop-2-enoate

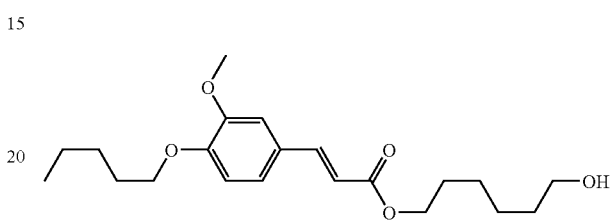

7.30 g (27.6 mmol) (2E)-3-[3-methoxy-4-(pentyloxy)phenyl]prop-2-enoic acid were suspended in 3 ml acetonitrile. A mixture of 4.20 g (27.6 mmol) 1,8-diazabicyclo[5.4.0]undec-7-ene(1,5-5) (DBU) and 3 ml acetonitrile was added dropwise over a period of 5 minutes. 3.43 g (25.1 mmol) 6-chlorohexanol were added and the resulting mixture was then refluxed for 6 hours. The reaction mixture was cooled and then extracted using ethyl acetate and water. The ethyl acetate phase was washed with water, dried over sodium sulphate, filtered and concentrated by rotary evaporation. Chromatography of the residue using a silica gel column yield 6-hydroxyhexyl (2E)-3-[3-methoxy-4-(pentyloxy)phenyl]prop-2-enoate.

Preparation of bis[6-({(2E)-3-[3-methoxy-4-(pentyloxy)phenyl]prop-2-enoyl}oxy)hexyl]malonate

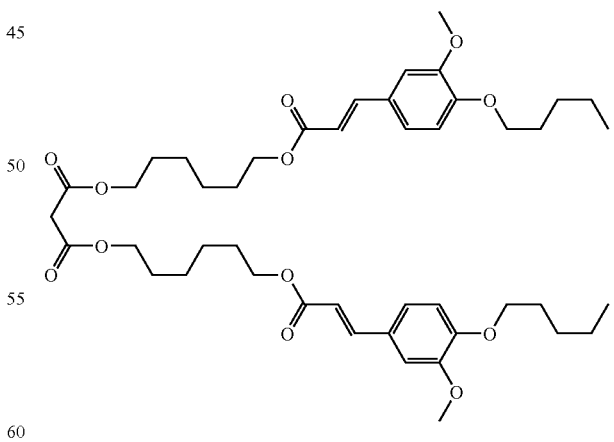

Preparation can be carried out analogously to Synthetic Example 1 using 5.00 g (13.7 mmol) 6-hydroxyhexyl (2E)-3-[3-methoxy-4-(pentyloxy)phenyl]prop-2-enoate and 0.86 g (8.26 mmol) malonic acid to yield bis[6-({(2E)-3-[3-methoxy-4-(pentyloxy)phenyl]prop-2-enoyl}oxy)hexyl]malonate.

Preparation of bis [8-({(2E)-3-[3-methoxy-4-(pentyloxy)phenyl)prop-2-enoyl}oxy)octyl]2,2-bis(nitrobenzyl)malonate

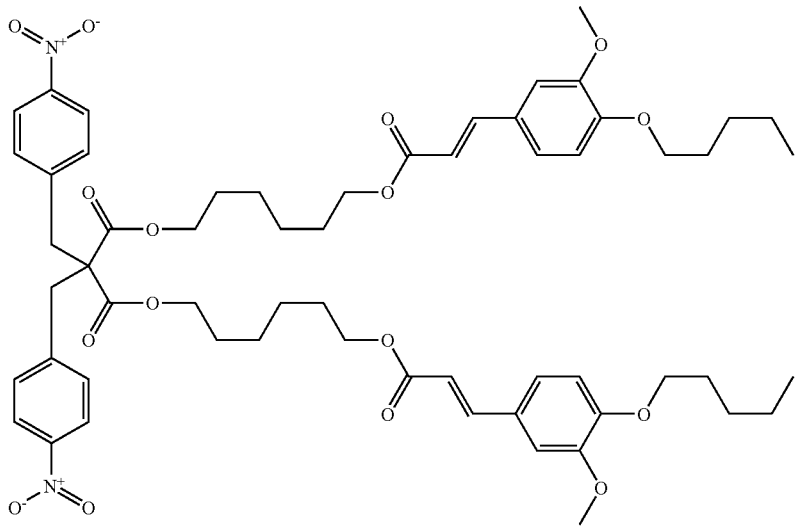

Preparation can be carried out analogously to Synthetic Example 1 using 0.80 g (1.00 mmol) bis[6-({(2E)-3-[3-methoxy-4-(pentyloxy)phenyl]prop-2-enoyl}oxy)hexyl]malonate, 0.42 g (2.00 mmol) 4-nitrobenzylbromide and 87 mg (2.00 mmol) sodium hydride 55% dispersion in mineral oil yield bis [8-({(2E)-3-[3-methoxy-4-(pentyloxy)phenyl)prop-2-enoyl}oxy)octyl]2,2-bis(nitrobenzyl)malonate.

Preparation of bis [8-({(2E)-3-[3-methoxy-4-(pentyloxy)phenyl)prop-2-enoyl}oxy)octyl]2,2-bis(aminobenzyl)malonate

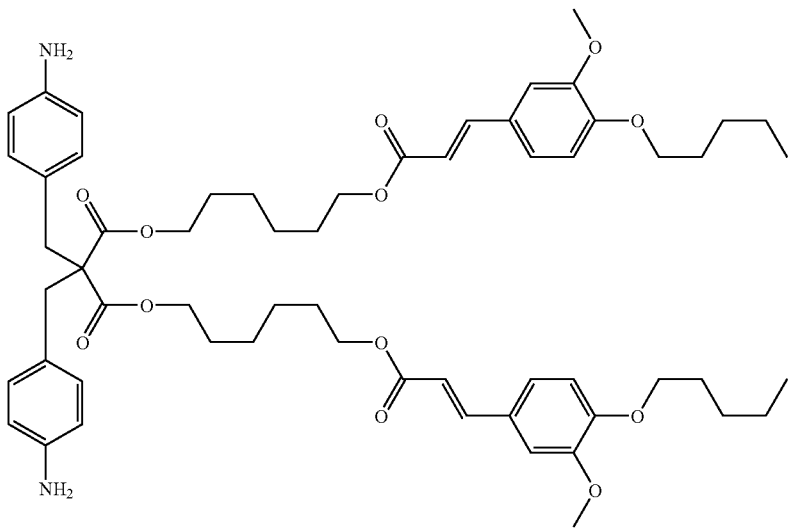

Preparation can be carried out analogously to Synthetic Example 1 using 1.07 g (1.00 mmol) of bis [8-({(2E)-3-[3-methoxy-4-(pentyloxy)phenyl)prop-2-enoyl}oxy)octyl]2,2-bis(nitrobenzyl)malonate, 1.62 g (6.00 mmol) Ferric chloride hexahydrate and 0.65 g (10.00 mmol) Zinc powder yield bis [8-({(2E)-3-[3-methoxy-4-(pentyloxy)phenyl)prop-2-enoyl}oxy)octyl]2,2-bis(aminobenzyl)malonate.

The following diamines can be synthesized in a analogous manner:

bis [8-({(2E)-3-[3-methoxy-4-(methoxy)phenyl)prop-2-enoyl}oxy)octyl]2,2-bis(aminobenzyl)malonate, bis [11-({(2E)-3-[4-(methoxy)phenyl)prop-2-enoyl}oxy)undecyl]2,2-bis(aminobenzyl)malonate, bis [6-({(2E)-3-[3-methoxy-4-(ethoxy)phenyl)prop-2-enoyl}oxy)hexyl]2,2-bis(aminobenzyl)malonate, bis [8-({(2E)-3-[3-pentyloxy-4-(methoxy)phenyl)prop-2-enoyl}oxy)octyl]2,2-bis(aminobenzyl)malonate, bis [4-({(2E)-3-[3-methoxy-4-(methoxy)phenyl)prop-2-enoyl}oxy)butyl]2,2-bis(aminobenzyl)malonate, bis [8-({(2E)-3-[4-(ethoxy)phenyl)prop-2-enoyl}oxy)octyl] 2,2-bis(aminobenzyl)malonate, bis [8-({(2E)-3-[4-(propyl)phenyl)prop-2-enoyl}oxy)octyl] 2,2-bis(aminobenzyl)malonate, and bis [6-({(2E)-3-[phenyl-prop-2-enoyl}oxy)hexyl]2,2-bis (aminobenzyl)malonate.

SYNTHESIS EXAMPLE 6

2,2-bis(4-aminobenzyl)-1,3-di {6-[4-(trans-4-propylcyclohexyl)phenoxy]hexanoyl}propanediol was prepared in accordance with the following procedure.

Preparation of 2,2-bis(4-nitrobenzyl)-1,3-di {6-[4-(trans-4-propylcyclohexyl)phenoxy] hexanoyl}propanediol

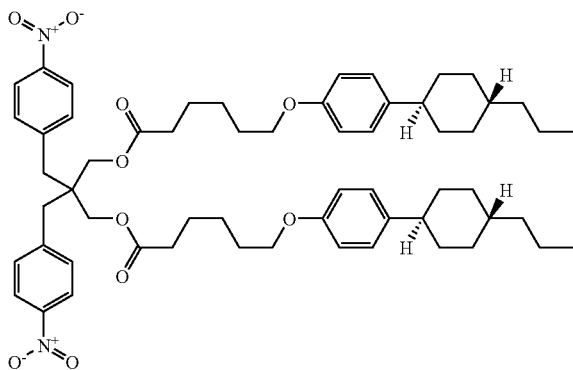

The preparation was carried out analogously to Synthesis Example 4 using 3.14 g (4.48 mmol) 2,2-bis(4-nitrobenzyl)-1,3 di(6-bromohexanoyl)propanediol and 1.96 g (8.98 mmol 4-(trans-4-propylcyclohexyl)phenol yield 2,2-bis(4-nitrobenzyl)-1,3-di {6-[4-(trans-4-propylcyclohexyl)phenoxy] hexanoyl}propanediol.

Preparation of 2,2-bis(4-aminobenzyl)-1,3-di {6-[4-(trans-4-propylcyclohexyl)phenoxy] hexanoyl}propanediol

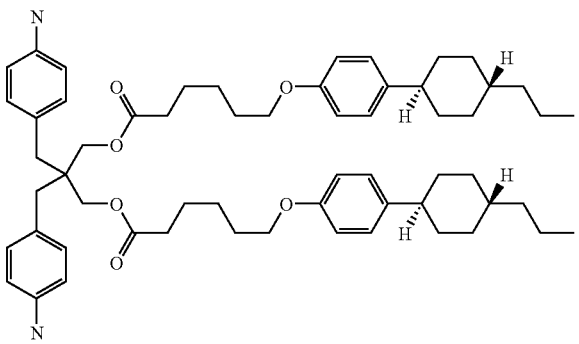

Preparation can be carried out analogously to Synthetic Example 1 using 0.975 g (1.00 mmol) 2,2-bis(4-nitrobenzyl)-1,3-di {6-[4-(trans-4-propylcyclohexyl)phenoxy] hexanoyl}propanediol, 1.62 g (6.00 mmol) Ferric chloride hexahydrate and 0.65 g (10.00 mmol) Zinc powder yield 2,2-bis(4-aminobenzyl)-1,3-di {6-[4-(trans-4-propylcyclohexyl)phenoxy]hexanoyl}propanediol.

SYNTHESIS EXAMPLE 7

Polymer 99.0 mg (0.505 mmol) of 1,2,3,4-cyclobutantetracarboxylic acid dianhydride was added to a solution of 500.0 mg (0.561 mmol) of bis [6-({4-[(1E)-3-methoxy-3-oxoprop-1-enyl]benzoyl}oxy)hexyl]2,2-bis(aminobenzyl)malonate in 3.5 ml of tetrahydrofuran. Stirring was then carried out at 0° C. for 2 hours. Then another 11.0 mg (0.056 mmol) of 1,2,3, 4-cyclobutantetracarboxylic acid dianhydride were added. The mixture was subsequently allowed to react for 21 hours at room temperature. The polymer mixture was diluted with 3.5 ml THF, precipitated into 200 ml diethyl ether and collected by filtration. The polymer was reprecipitated form THF (10 ml) into 600 ml water to yield, after drying at room temperature under vacuum, 0.57 g of Polyamic Acid 1 in the from of a white powder; [η]=1.66 dL/g.

SYNTHESIS EXAMPLE 8

Polymer

The preparation was carried out analogously to Synthesis Example 7 using 500.0 mg (0.561 mmol) of bis [6-({4-[(1E)-3-methoxy-3-oxoprop-1-enyl]-benzoyl}oxy)hexyl]2,2-bis (aminobenzyl)malonate and 158.5 mg (0.561 mmol) of 4-(2, 5-Dioxotetrahydrofuran-3-yl)-tetralin-1,2-dicarboxylic anhydride; it yielded 0.60 g Polyamic acid 2 in the form of a white powder; [η]=0.27 dL/g.

SYNTHESIS EXAMPLE 9

Polymer

The preparation was carried out analogously to Synthesis Example 7 using 500.0 mg (0.561 mmol) of bis [6-({4-[(1E)-3-methoxy-3-oxoprop-1-enyl]-benzoyl}oxy)hexyl]2,2-bis (aminobenzyl)malonate and 139.5 mg (0.561 mmol) of 5-(2, 5-Dioxotetrahydrofuryl)-3-methyl-3-cyclohexen-1,2-dicarboxylic anhydride; it yielded 0.60 g Polyamic acid 3 in the form of a white powder; [η]=0.31 dL/g.

SYNTHESIS EXAMPLE 10

Polymer

The preparation was carried out analogously to Synthesis Example 7 using 500.0 mg (0.895 mmol) 6-({4-[(1E)-3-methoxy-3-oxoprop-1-enyl]benzoyl}-oxy)hexyl 2-(4-aminobenzyl)-3-(4-aminophenyl) propanoate and 175.5 mg (0.895 mmol) 1,2,3,4-cyclobutantetracarboxylic acid dianhydride; it yielded 0.61 g of white Polyamic acid 4; [η]=1.72 dL/g.

SYNTHESIS EXAMPLE 11

Polymer

The preparation was carried out analogously to Synthesis Example 7 using 225.1 mg (0.565 mmol) isopropyl 2,2-bis (aminobenzyl)malonate, 250.0 mg (0.565 mmol) 6-({4-

[(1E)-3-methoxy-3-oxoprop-1-enyl]benzoyl}oxy)hexyl 3,5-diaminobenzoate and 221.6 mg (1.017 mmol) 1,2,3,4-cyclobutantetracarboxylic acid dianhydride to yield 0.66 g of white Polyamic acid 5; [η]=2.06 dL/g.

SYNTHESIS EXAMPLE 12

Polymer

The preparation was carried out analogously to Synthesis Example 7 using 500.0 mg (0.528 mmol) bis[8-({4-[(1E)-3-methoxy-3-oxoprop-1-enyl]benzoyl}oxy)octyl]2,2-bis(4-aminobenzyl)malonate and 103.5 mg (0.528 mmol) 1,2,3,4-cyclobutantetracarboxylic acid dianhydride; it yielded 0.58 g of white Polyamic acid 6; [η]=1.36 dL/g.

SYNTHESIS EXAMPLE 13

Polymer

The preparation was carried out analogously to Synthesis Example 7 using 500.0 mg (0.544 mmol) bis[6-({4-[(1E)-3-ethoxy-3-oxoprop-1-enyl]benzoyl}oxy)hexyl]2,2-bis(4-aminobenzyl)malonate and 106.7 mg (0.544 mmol) 1,2,3,4-cyclobutantetracarboxylic acid dianhydride yielded 0.58 g of white Polyamic acid 7; [η]=0.79 dL/g.

SYNTHESIS EXAMPLE 14

Polymer

The preparation was carried out analogously to Synthesis Example 7 using 450.0 mg (0.539 mmol) bis[6-(4-[(1E)-3-methoxy-3-oxoprop-1-enyl]phenoxy)hexyl]2,2-bis(4-aminobenzyl)malonate and 105.7 mg (0.539 mmol) 1,2,3,4-cyclobutantetracarboxylic acid dianhydride yielded 0.55 g of white Polyamic acid 8; [η]=1.30 dL/g.

SYNTHESIS EXAMPLE 15

Polymer

The preparation was carried out analogously to Synthesis Example 7 using 450.0 mg (1.022 mmol) 6-({4-[(1E)-3-methoxy-3-oxoprop-1-enyl]benzoyl}oxy)hexyl 3,5-diaminobenzoate, 72.5 mg (0.113 mmol) Cholest-5-en-3-yl 2-(4-aminobenzyl)-3-(4-aminophenyl)propanoate and 222.6 mg (1.135 mmol) 1,2,3,4-cyclobutantetracarboxylic acid dianhydride to yield 0.70 g of white Polyamic Acid 9; [η]=0.48 dL/g.

SYNTHESIS EXAMPLE 16

Polymer

The preparation was carried out analogously to Synthesis Example 7 using 500.0 mg (0.599 mmol) 2,2-bis(4-aminobenzyl)-1,3 di(6-{4-[(1E)-3-methoxy-3-oxoprop-1-enyl]phenoxy}hexanoyl)propanediol and 117.4 mg (0.599 mmol) 1,2,3,4-cyclobutantetracarboxylic acid dianhydride to yield 0.70 g of white Polyamic Acid 10; [η]=1.65 dL/g.

SYNTHESIS EXAMPLE 17

Polymer

The preparation was carried out analogously to Synthesis Example 7 using 250.0 mg (0.567 mmol) 6-({4-[(1E)-3-methoxy-3-oxoprop-1-enyl]benzoyl}oxy)hexyl 3,5-diaminobenzoate, 505.7 mg (0.567 mmol) bis [6-({4-[(1E)-3-methoxy-3-oxoprop-1-enyl]benzoyl}oxy)hexyl]2,2-bis(aminobenzyl)malonate and 222.6 mg (1.135 mmol) 1,2,3,4-cyclobutantetracarboxylic acid dianhydride to yield 0.93 g Polyamic Acid 11; [η]=0.80 dL/g.

SYNTHESIS EXAMPLE 18

Polymer 0.40 g of polyamic acid 1 obtained in Synthesis Example 7 were dissolved in 3 ml of tetrahydrofurane. Thereto were added 73 mg (0.92 mmol) of pyridine and 94 mg (0.92 mmol) acetic acid anhydride, and the dehydration and ring closure was carried out at reflux temperature for 2 hours. The polymer mixture was diluted with 1.5 ml THF, precipitated into 100 ml diethyl ether and collected by filtration. The polymer was reprecipitated form THF (10 ml) into 200 ml water to yield, after drying at room temperature under vacuum, Polyimide 1.

Example for the Production of an Orientation Layer for Liquid Crystals

A 2% solution of Polyamic acid 1 in cyclopentanone was filtered over a 0.2 μm Teflon filter and applied to a glass plate, which had been coated with indium-tin oxide (ITO), in a spin-coating apparatus at 3000 rev./min. in the course of 60 seconds. The resulting film was then predried for 15 minutes at 130° C. and then imidized for 1 hour at 200° C. to form a polyimide film.

The coating on the glass plate was then irradiated for 3 minutes with the linearly polarized UV light of a 350 W high-pressure mercury vapour lamp.

To verify the ability of the thus produced film to orient liquid crystals, a liquid-crystalline mixture of diacrylates was applied unto the film layer by spin-coating and subsequently crosslinked by isotropic UV light for 5 minutes. Under a polarization microscope, a uniaxially double-refractive layer of oriented liquid crystal molecules was observed and a contrast ratio as high as 400:1 was measured. Using a tilt compensator it was ascertained that the direction of orientation agreed with the direction of polarisation of the UV light used for the polymer layer irradiation.

Example for the Determination of the Voltage Holding Ratio (VHR)

Two glass plates coated in accordance with the procedure described in the above Example were irradiated perpendicularly during 4 minutes with linearly polarized UV light. From the two plates a cell of 10 μm spacing was built such that the illuminated surfaces were facing each other and the previous polarization directions of illumination were parallel. This cell was then maintained at 120° C. under high vacuum for 14 hours and thereafter filled with TFT liquid crystal mixture MLC12000-000 from Merck in vacuum at room temperature.

Between crossed polarizers a uniformly oriented liquid crystal layer was observed. Prior to testing the voltage holding ratio (VHR), the cell was first subjected to ageing for 50 hours at 120° C. The voltage decay V (at T=20 ms) of a voltage surge of 64 μs with $V_0$ (V at t=0)=0.2 V was then measured over a period of T=20 ms. The voltage holding ratio then determined, given by VHR=$V_{rms}(t=T)/V_0$, was 97%.

Example for the Determination of Image Sticking

From two glass plates prepared as described above, a cell of 5 μm spacing was built such that the illuminated surfaces were facing each other and the previous polarization directions of illumination were perpendicular. This TN cell was then filled with liquid crystal mixture MLC12000-000 from Merck in vacuum at room temperature. Between crossed polarizers an uniformly oriented liquid crystal layer was observed.

The above described TN cell was placed between crossed polarizers, illuminated with a 50 W conventional halogen lamp running at 12 V and the optical transmission was monitored using a photodiode. The cell was mounted on a thermostatised holder and the temperature was kept at 50° C. during the whole experiment. The resulting signal was transferred onto a PC data acquisition board and the optical transmission as a function of time was used as a direct measurement of the effective voltage $V_{\mathit{eff}}$ across the pixel of the liquid crystal test cell. The applied wave form was divided into two periods:
—During period t1 (adsorption of ions, duration 3600 seconds) a DC offset voltage of 1 volt was superposed to an AC detection square wave running at a frequency of 1000 Hz; the AC detection signal was approximately $V_{50}$ (i.e. voltage at 50% of the optical transmission) of the transmission-voltage curve. —During period t2 (desorption of ions, duration 6400 seconds) no DC offset voltage was applied and only the AC detection signal was monitored.

The TN cell showed in the adsorption period t1 a deviation of $V_{\mathit{eff}}$ of 56 mV whereas in the desorption period t2 no deviation in the $V_{\mathit{eff}}$ signal was to be detected.

The invention claimed is:

1. Diamine compounds represented by the general formula I:

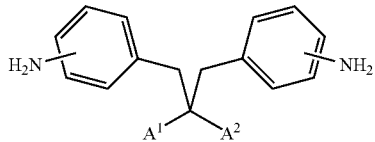

wherein $A^1$ and $A^2$ each independently represent a mesogen group represented by general formula II:

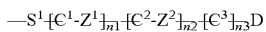

wherein $C^1$ to $C^3$ each independently represent an aromatic or an alicyclic group, which is unsubstituted or mono- or poly-substituted by a cyano group or by halogen atoms, or by a cyclic, straight-chain or branched alkyl residue which is unsubstituted, mono- or poly-substituted by fluorine, chlorine, having 1 to 18 carbon atoms, or by a cyclic, straight-chain or branched alkyl residue which is unsubstituted, mono- or poly-substituted by fluorine, chlorine, having 1 to 18 carbon atoms, wherein one or more non-adjacent —$CH_2$— groups is independently replaced by a group B;

D represents a hydrogen atom, a halogen atom, a cyano group, or a straight-chain or branched alkyl residue which is unsubstituted, mono-substituted by cyano or fluorine, chlorine, or poly-substituted by fluorine, chlorine, having 1 to 24 carbon atoms, or a straight-chain or branched alkyl residue which is unsubstituted, mono-substituted by cyano or fluorine, chlorine, or poly-substituted by fluorine, chlorine, having 1 to 24 carbon atoms, wherein one or more non-adjacent —$CH_2$- groups is independently replaced by a group B, or represents a organic group having a steroid skeleton;

$S^1$ represents 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 2-(methylenoxy)ethylene, 3-(methylenoxy)propylene, 4-(methylenoxy)butylene, 5-(methylenoxy)pentylene, 6-(methylenoxy)hexylene, 7-(methylenoxy)heptylene, 8-(methylenoxy)octylene, 9-(methylenoxy)nonylene, 10-(methylenoxy)decylene, 11-(methylenoxy)undecylene, 12-(methylenoxy)dodecylene, 2-(carbonyloxy)ethylene, 3-(carbonyloxy)propylene, 4-(carbonyloxy)butylene, 5-(carbonyloxy)pentylene, 6-(carbonyloxy)hexylene, 7-(carbonyloxy)heptylene, 8-(carbonyloxy)octylene, 9-(carbonyloxy)nonylene, 10-(carbonyloxy)decylene, 11-(carbonyloxy)undecylene, 12-(carbonyloxy)dodecylene, 2-(carbonylamino)ethylene, 3-(carbonylamino)propylene, 4-(carbonylamino)butylene, 5-(carbonylamino)pentylene, 6-(carbonylamino)hexylene, 7-(carbonylamino)heptylene, 8-(carbonylamino)octylene, 9-(carbonylamino)nonylene, 10-(carbonylamino)decylene, 11-(carbonylamino)undecylene, 12-(carbonylamino)dodecylene, 3-propyleneoxy, 3-propyleneoxycarbonyl, 2-ethylenoxyloxy, 4-butyleneoxy, 4-butyleneoxycarbonyl, 3-propylenoyloxy, 5-pentyleneoxy, 5-pentyleneoxycarbonyl, 4-butylenoyloxy, 6-hexyleneoxy, 6-hexyleneoxycarbonyl, 5-pentylenoyloxy, 7-heptyleneoxy, 7-heptyleneoxycarbonyl, 6-hexylenoyloxy, 8-octyleneoxy, 8-octyleneoxycarbonyl, 7-heptylenoyloxy, 9-nonyleneoxy, 9-nonyleneoxycarbonyl, 8-octylenoyloxy, 10-decyleneoxy, 10-decyleneoxycarbonyl, 9-nonylenoyloxy, 11-undecyleneoxy, 11-undecyleneoxycarbonyl, 10-decylenoyloxy, 12-dodecyleneoxy, 12-dodecyleneoxycarbonyl, 11-undecylenoyloxy, 3-propyleneaminocarbonyl, 4-butyleneaminocarbonyl, 5-pentyleneaminocarbonyl, 6-hexyleneaminocarbonyl, 7-heptyleneaminocarbonyl, 8-octyleneaminocarbonyl, 9-nonyleneaminocarbonyl, 10-decyleneaminocarbonyl, 11-undecyleneaminocarbonyl, 12-dodecyleneaminocarbonyl, 2-ethylenecarbonylamino, 3-propylenecarbonylamino, 4-butylenecarbonylamino, 5-pentylenecarbonylamino, 6-hexylenecarbonylamino, 7-heptylenecarbonylamino, 8-octylenecarbonylamino, 9-nonylenecarbonylamino, 10-decylenecarbonylamino, 11-undecylenecarbonylamino, 2-(methylenoxy)ethanoyloxy, 3-(methylenoxy)propyloxy, 3-(methylenoxy)propyloxycarbonyl, 4-(methylenoxy)butyloxy, 4-(methylenoxy)butyloxycarbonyl, 3-(methylenoxy)propanoyloxy, 5-(methylenoxy)pentyloxy, 5-(methylenoxy)pentyloxycarbonyl, 4-(methylenoxy)butanoyloxy, 6-(methylenoxy)hexyloxy, 6-(methylenoxy)hexyloxycarbonyl, 5-(methylenoxy)pentanoyloxy, 7-(methylenoxy)heptyloxy, 7-(methylenoxy)heptyloxycarbonyl, 6-(methylenoxy)hexanoyloxy, 8-(methylenoxy)octyloxy, 8-(methylenoxy)octyloxycarbonyl, 7-(methylenoxy)heptanoyloxy, 9-(methylenoxy)nonyloxy, 9-(methylenoxy)nonyloxycarbonyl, 8-(methylenoxy)octanoyloxy, 10-(methylenoxy)decyloxy, 10-(methylenoxy)decyloxycarbonyl, 9-(methylenoxy)nonanoyloxy, 11-(methylenoxy)undecyloxy, 11-(methylenoxy)undecyloxycarbonyl, 10-(methylenoxy)decanoyloxy, 12-(methylenoxy)dodecyloxy, 12-(methylenoxy)dodecyloxycarbonyl, 11-(methylenoxy)undecanoyloxy, 3-(methylenoxy)propylaminocarbonyl, 4-(methylenoxy)butylaminocarbonyl, 5-(methylenoxy)pentylaminocarbonyl, 6-(methylenoxy)hexylaminocarbonyl, 7-(methylenoxy)heptylaminocarbonyl, 8-(methylenoxy)octylaminocarbonyl, 9-(methylenoxy)nonylaminocarbonyl, 10-(methylenoxy)

decylaminocarbonyl, 11-(methylenoxy)undecylaminocarbonyl, 12-(methylenoxy)dodecylaminocarbonyl, 2-(methylenoxy)ethanoylamino, 3-(methylenoxy)propanoylamino, 4-(methylenoxy)butanoylamino, 5-(methylenoxy)pentanoylamino, 6-(methylenoxy)hexanoylamino, 7-(methylenoxy)heptanoylamino, 8-(methylenoxy)octanoylamino, 9-(methylenoxy)nonanoylamino, 10-(methylenoxy)decanoylamino, 11-(methylenoxy)undecanoylamino, 12-(methylenoxy)dodecylaminocarbonyl, 2-(carbonyloxy)ethanoyloxy, 3-(carbonyloxy)propyloxy, 3-(carbonyloxy)propyloxycarbonyl, 4-(carbonyloxy)butyloxy, 4-(carbonyloxy)butyloxycarbonyl, 3-(carbonyloxy)propanoyloxy, 5-(carbonyloxy)pentyloxy, 5-(carbonyloxy)pentyloxycarbonyl, 4-(carbonyloxy)butanoyloxy, 6-(carbonyloxy)hexyloxy, 6-(carbonyloxy)hexyloxycarbonyl, 5-(carbonyloxy)pentanoyloxy, 7-(carbonyloxy)heptyloxy, 7-(carbonyloxy)heptyloxycarbonyl, 6-(carbonyloxy)hexanoyloxy, 8-(carbonyloxy)octyloxy, 8-(carbonyloxy)octyloxycarbonyl, 7-(carbonyloxy)heptanoyloxy, 9-(carbonyloxy)nonyloxy, 9-(carbonyloxy)nonyloxycarbonyl, 8-(carbonyloxy)octanoyloxy, 10-(carbonyloxy)decyloxy, 10-(carbonyloxy)decyloxycarbonyl, 9-(carbonyloxy)nonanoyloxy, 11-(carbonyloxy)undecyloxy, 11-(carbonyloxy)undecyloxycarbonyl, 10-(carbonyloxy)decanoyloxy, 12-(carbonyloxy)dodecyloxy, 12-(carbonyloxy)dodecyloxycarbonyl, 11-(carbonyloxy)undecanoyloxy, 3-(carbonyloxy)propylaminocarbonyl, 4-(carbonyloxy)butylaminocarbonyl, 5-(carbonyloxy)pentylaminocarbonyl, 6-(carbonyloxy)hexylaminocarbonyl, 7-(carbonyloxy)heptylaminocarbonyl, 8-(carbonyloxy)octylaminocarbonyl, 9-(carbonyloxy)nonylaminocarbonyl, 10-(carbonyloxy)decylaminocarbonyl, 11-(carbonyloxy)undecylaminocarbonyl, 12-(carbonyloxy)dodecylaminocarbonyl, 2-(carbonyloxy)ethanoylamino, 3-(carbonyloxy)propanoylamino, 4-(carbonyloxy)butanoylamino, 5-(carbonyloxy)pentanoylamino, 6-(carbonyloxy)hexanoylamino, 7-(carbonyloxy)heptanoylamino, 8-(carbonyloxy)octanoylamino, 9-(carbonyloxy)nonanoylamino, 10-(carbonyloxy)decanoylamino, 11-(carbonyloxy)undecanoylamino, 12-(carbonyloxy)undecylaminocarbonyl 6-(3-propyleneaminocarbonyloxy)hexylene, 6-(3-propyleneoxy)hexylene, 6-(3-propyleneoxy)hexyloxy, 6-(3-propyleneaminocarbonyloxy)hexyloxy, 6-(3-propyleneaminocarbonyl)hexyl, 6-(3-propyleneaminocarbonyl)hexyloxy, 2-(1-methyleneoxy)ethyloxycarbonyloxy, 3-(1-methyleneoxy)propyloxycarbonyloxy, 6-(1-methyleneoxy)hexyloxycarbonyloxy, 2-(1-methyleneoxycarbonyl)ethylene, 3-(1-methyleneoxycarbonyl)propyloxycarbonyloxy, 6-(1-methyleneoxycarbonyl)hexyloxycarbonyloxy, 6-(3-propyleneoxycarbonyloxy)hexylene, 6-(3-propyleneoxycarbonyl)hexylene, 2-(1-methyleneaminocarbonyl)ethylene, 3-(1-methyleneaminocarbonyl)propylene, 6-(1-methyleneaminocarbonyl)hexylene, and 6-(3-propyleneaminocarbonyloxy)hexylene, 6-(3-propyleneaminocarbonyl)hexylene.

Z1, Z2 each independently of the other represent a single bond or a spacer unit which is straight-chain or branched alkylene group which is unsubstituted, mono or polysubstituted by a cyano group or by halogen atoms, having 1 to 8 carbon atoms or a spacer unit such a straight-chain or branched alkylene group which is unsubstituted, mono or poly-substituted by a cyano group or by halogen atoms, having 1 to 8 carbon atoms, wherein one or more non-adjacent —CH$_2$— groups is independently replaced by a group B;

n1 is 0 or 1, and n2 and n3 are 1; and

B represents a group selected from —O—, —CO—, —CO—O—, —O—CO—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C—, —O—CO—O— and —Si(CH$_3$)$_2$—O—Si(CH$_3$)$_2$— and wherein R$^1$ represents a hydrogen atom or a straight chain or branched hydrocarbon radical having from 1 to 6 carbon atoms.

2. Diamine compounds according to claim 1, wherein C$^1$ to C$^3$ are selected from pyrimidine-2,5-diyl, pyridine-2,5-diyl, 1,4- or 2,6-naphthylene, decahydronaphthalin-2,6-diyl, 1,2,3,4-tetrahydronaphthalin-2,6-diyl, cyclohexane-1,4-diyl and 1,4-phenylene, which is unsubstituted or substituted by a cyclic, straight-chain or branched alkyl residue which is unsubstituted, mono- or poly-substituted by fluorine, chlorine having from 1 to 12 carbon atoms in which optionally one or more non-adjacent —CH$_2$— groups are replaced by —O—, —CO—, —CO—O—, —O—CO—, —CH=CH— and —C≡C—.

3. Diamine compounds according to claim 1, wherein C$^1$ to C$^3$ are selected from cyclohexane-1,4-diyl and 1,4-phenylene, which is unsubstituted or substituted by a cyclic, straight-chain or branched alkyl residue having 1 to 12 carbon atoms in which optionally one or more non-adjacent —CH$_2$— groups are replaced by —O—, —CO—, —CO—O—, —O—CO—, —CH=CH— and —C≡C—.

4. Diamine compounds according to claim 1, wherein D is a hydrogen atom, a fluoro atom, a chloro atom, a cyano group, a straight-chain or branched alkyl residue which is unsubstituted, mono-substituted by cyano or fluorine, chlorine, or polysubstituted by fluorine, chlorine, having 1 to 18 carbon atoms or a straight-chain or branched alkyl residue which is unsubstituted, mono-substituted by cyano or fluorine, chlorine, or poly-substituted by fluorine, chlorine, having 1 to 18 carbon atoms, wherein one or more non-adjacent-CH$_2$— groups is independently replaced by —O—, —CO—, —CO—O—, —O—CO—, —NR$^1$—CO—, —CO—NR$^1$—, —NR$^1$—CO—O—, —O—CO—NR$^1$—, —CH=CH—, —C≡C— and —O—CO—O—, wherein R$^1$ represents a hydrogen atom or a straight chain or branched hydrocarbon radical having from 1 to 6 carbon atoms, or represents an organic group having a steroid skeleton.

5. Diamine compounds according to claim 1, wherein D is a hydrogen atom, a fluoro atom, a chloro atom, a cyano group, a straight-chain or branched alkyl residue, having 1 to 12 carbon atoms or a straight-chain or branched alkyl residue, having 1 to 12 carbon atoms, wherein one or more non-adjacent —CH$_2$— groups is independently replaced by —O—, —CO—, —CO—O—, —O—CO—, —CH=CH—, —C≡C— and —O—CO—O—.

6. Diamine compounds according to claim 1, wherein S$^1$ is selected from a single covalent bond, —CO—O—, —CO—NR$^1$—, —CO—, a straight-chain or branched alkylene group which is unsubstituted, mono or poly-substituted by fluorine, chlorine and cyano, having 1 to 24 carbon atoms, and a straight-chain or branched alkylene group which is unsubstituted, mono or poly-substituted by fluorine, chlorine and cyano, having 1 to 24 carbon atoms, wherein one or more non-adjacent —CH$_2$— groups is independently replaced by a group B, wherein $R^1$ represents a hydrogen atom or a straight chain or branched hydrocarbon radical having from 1 to 6 carbon atoms.

7. Diamine compounds according to claim 1, wherein S1 is selected from a single covalent bond, —CO—O—, —CO—, —(CH$_2$)$_r$—, —(CH$_2$)$_r$—O—, —(CH$_2$)$_r$—CO—, —(CH$_2$)$_r$—CO—O—, —(CH$_2$)$_r$—O—CO—, —(CH$_2$)$_r$—CO—NR$^1$—, —(CH$_2$)$_r$—NR$^1$—CO—, —(CH$_2$)$_r$—NR$^1$—, —CO—O—(CH$_2$)$_r$—, —CO—NR$^1$—(CH$_2$)$_r$—, —CO—O—(CH$_2$)$_r$—O—, —CO—NR$^1$—(CH$_2$)$_r$—O—, —CO—NR$^1$—(CH$_2$)$_r$—NR$^1$—, —CO—NR$^1$—(CH$_2$)$_r$—O—CO—, —(CH$_2$)$_r$—O—(CH$_2$)$_s$—, —(CH$_2$)$_r$—CO—O—(CH$_2$)$_s$—, —(CH$_2$)$_r$—O—CO—(CH$_2$)$_s$—, —(CH$_2$)$_r$—NR$^1$—CO—(CH$_2$)$_s$—, —(CH$_2$)$_r$—NR$^1$—CO—O—(CH$_2$)$_s$—, —(CH$_2$)$_r$—O—(CH$_2$)$_s$—O—, —(CH$_2$)$_r$—CO—O—(CH$_2$)$_s$—O—, —(CH$_2$)$_r$—O—CO—(CH$_2$)$_s$—O—, —(CH$_2$)$_r$—NR$^1$—CO—(CH$_2$)$_s$—O—, —(CH$_2$)$_r$—NR$^1$—CO—O-(CH$_2$)$_s$—O—, —CO—O—(CH$_2$)$_r$—O—(CH$_2$)$_s$— and —CO—O(CH$_2$)$_r$—O—(CH$_2$)$_s$—O—, wherein $R^1$ is defined above, r and s each represent an integer from 1 to 20 and r+s≦21.

8. Diamine compounds according to claim 1, wherein $S^1$ is selected from a single covalent bond, —(CH$_2$)$_r$—, —(CH$_2$)$_r$—O—, —(CH$_2$)$_r$—CO—O—, —(CH$_2$)$_r$—O—CO—, —(CH$_2$)$_r$—CO—NH—, —(CH$_2$)$_r$—NH—CO—, —CO—O—(CH$_2$)$_r$—, —CO—NH—(CH$_2$)$_r$—, —CO—O—(CH$_2$)$_r$—O—, —CO—NH—(CH$_2$)$_r$—O—, —(CH$_2$)$_r$—NH—CO—(CH$_2$)$_s$—, —(CH$_2$)$_r$—NH—CO—O—(CH$_2$)$_s$—, —(CH$_2$)$_r$—O—(CH$_2$)$_s$—O—, —(CH$_2$)$_r$—NH—CO—(CH$_2$)$_s$—O—, —(CH$_2$)$_r$—NHCO—O—(CH$_2$)$_s$—O—, —CO—O—(CH$_2$)$_r$—O—(CH$_2$)$_s$—O—, and —CO—(CH$_2$)$_r$—NH—CO—(CH$_2$)$_s$—O—, wherein r and s each represent an integer from 1 to 12 and r+s≦15.

9. Diamine compounds according to claim 1, wherein $Z^1$ and $Z^2$ are selected from a single covalent bond, a spacer unit such as a straight-chain or branched alkylene group, which is unsubstituted, mono or poly-substituted by fluoro atoms, having 1 to 8 carbon atoms, and a spacer unit which is a straight-chain or branched alkylene group, which is unsubstituted, mono or poly-substituted by fluoro atoms, having 1 to 8 carbon atoms, wherein one or more non-adjacent —CH$_2$— groups is independently replaced by a group selected from —O—, —CO—, —CO—O—, —O—CO—, —NR$^1$—CO—, —CO—NR$^1$—, —CH═CH—, —C≡C—, and wherein $R^1$ represents a hydrogen atom or a straight chain or branched hydrocarbon radical having from 1 to 6 carbon atoms.

10. Diamine compounds according to claim 1, wherein $Z^1$ and $Z^2$ are selected from a single covalent bond, a spacer unit such a straight-chain or branched alkylene group having 1 to 4 carbon atom, and a spacer unit which is straight-chain or branched alkylene group having 1 to 4 carbon atoms, wherein one or two non-adjacent —CH$_2$— groups is independently replaced by a group selected from —O—, —CO—, —CO—O—, —O—CO—.

11. Diamine compounds according to claim 1, wherein n1=0 with n2=1 and n3=1.

12. Diamine compounds according to claim 1, wherein the steroid skeleton is a 3-cholesteryl or a 3-cholestanyl residue.

13. Diamine compounds according to claim 1, wherein $A^1$ and $A^2$ each independently represent a photoreactive group which can be photoisomerized on exposure to UV or laser light, wherein the photoreactive groups include cinnamates, benzylidenephthalimidines, benzylideneacetophones, diphenylacetylenes stilbazoles, uracyl, quinolinone, maleinimides, or cinnamylidene acetic acid derivatives.

14. Diamine compounds according to claim 1, wherein $A^1$ and $A^2$ each independently represent a photoreactive group which can be photoisomerized on exposure to UV or laser light, wherein the photoreactive groups are represented by general formulae IIIa and IIIb:

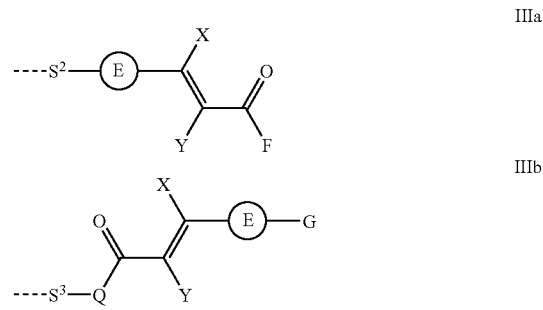

wherein
E represents pyrimidine-2,5-diyl, pyridine-2,5-diyl, 2,5-thiophenylene, 2,5-furanylene, 1,4- or 2,6-naphthylene, or phenylene, which is unsubstituted or mono- or poly-substituted by fluorine, chlorine, by a cyclic, straight-chain or branched alkyl residue which is unsubstituted, mono- or poly-substituted by fluorine, chlorine, having 1 to 18 carbon atoms, or by a cyclic, straight-chain or branched alkyl residue which is unsubstituted mono- or poly-substituted by fluorine, chlorine, having 1 to 18 carbon atoms, wherein one or more non-adjacent —CH$_2$— groups is independently be replaced by a group B as defined hereinabove;

F represents $OR^2$, —$NR^3R^4$ or an oxygen atom, which defines together with the ring B a coumarin unit, wherein $R^2$, $R^3$ and $R^4$ are selected from hydrogen, a cyclic, straight-chain or branched alkyl residue which is unsubstituted, mono- or poly-substituted by fluorine, chlorine, having 1 to 24 carbon atoms, a cyclic, straight-chain or branched alkyl residue which is unsubstituted, mono- or poly-substituted by fluorine, chlorine, having 1 to 24 carbon atoms, wherein one or more non-adjacent —CH$_2$— groups is independently replaced by a group J, or $R^3$ and $R^4$ together form a $C_{5-8}$ alicyclic ring; wherein J represents a group selected from —O—, —CO—, —CO—O—, —O—CO—, —NR$^1$—, —NR$^1$—CO—, —CO—NR$^1$—, —NR$^1$—CO—O—, —O—CO—NR$^1$—, —NR$^1$—CO—NR$^1$—, —CH═CH—, —C≡C—, —O—CO—O— and —Si(CH$_3$)$_2$—O—Si(CH$_3$)$_2$—, an aromatic or an alicyclic group, and wherein $R^1$ represents a hydrogen atom or a straight chain or branched hydrocarbon radical having from 1 to 6 carbon atoms;

G represents a hydrogen atom, or a halogen atom, a straight-chain or branched alkyl group which is unsubstituted, mono or poly-substituted by cyano, fluorine, chlorine, having 1 to 24 carbon atoms, or a straight-chain or branched alkyl group which is unsubstituted, mono or poly-substituted by cyano, fluorine, chlorine, having 1 to 24 carbon atoms, wherein one or more —CH$_2$— groups is independently replaced by a group J, with the proviso that oxygen atoms are not directly attached to each other;

$S^2$, $S^3$ each independently of the other represent a single bond, a spacer unit which is a straight-chain or branched alkylene group which is unsubstituted, mono or polysubstituted by fluorine, chlorine, or cyano, having 1 to 40 carbon atoms, or a spacer unit which is a straight-chain or branched alkylene group which is unsubstituted, mono or poly-substituted by fluorine, chlorine, or cyano, having 1 to 40 carbon atoms, wherein one or more —$CH_2$— groups is independently replaced by a group J, with the proviso that oxygen atoms are not directly attached to each other;

Q represents an oxygen atom or —$NR^1$— wherein $R^1$ represents a hydrogen atom or a straight chain or branched hydrocarbon radical having from 1 to 6 carbon atoms;

X, Y each independently of the other represents hydrogen, fluorine, chlorine, cyano, alkyl optionally substituted by fluorine having 1 to 12 carbon atoms in which optionally one or more non-adjacent alkyl —$CH_2$— groups are replaced by —O—, —CO—O—, —O—CO— and/or —CH=CH—.

15. Diamine compounds according to claim 14, wherein E is selected from pyrimidine-2,5-diyl, pyridine-2,5-diyl, 2,5-thiophenylene, 2,5-furanylene, 1,4- or 2,6-naphthylene and phenylene, which is unsubstituted or substituted by a cyclic, straight-chain or branched alkyl residue which is unsubstituted, mono- or poly-substituted by fluorine, chlorine having 1 to 12 carbon atoms in which optionally one or more non-adjacent alkyl —$CH_2$— groups are replaced by —O—, —CO—, —CO—O—, —O—CO—, —CH=CH— and —C≡C—.

16. Diamine compounds according to claim 14, wherein E is selected from 2,5-furanylene, 1,4- or 2,6-naphthylene and phenylene, which is unsubstituted or substituted by a cyclic, straight-chain or branched alkyl residue having 1 to 12 carbon atoms in which optionally one or more non-adjacent alkyl —$CH_2$— groups are replaced by —O—, —CO—, —CO—O—, —O—CO—, —CH=CH— and —C≡C—.

17. Diamine compounds according to claim 14, wherein F is selected from $OR^2$ and $NR^3R^4$, wherein $R^2$ and $R^3$ represent a cyclic, straight-chain or branched alkyl residue which is unsubstituted, mono- or poly-substituted by fluorine, chlorine, cyano, having 1 to 18 carbons atoms or a cyclic, straight-chain or branched alkyl residue which is unsubstituted, mono- or poly-substituted by fluorine, chlorine, cyano, having 1 to 18 carbons atoms, wherein one or more non-adjacent alkyl —$CH_2$— groups is independently replaced by —O— or —CH=CH—, wherein $R^4$ is selected from a hydrogen atom, a cyclic, straight-chain or branched alkyl residue which is unsubstituted, mono- or poly-substituted by fluorine, chlorine, cyano, having 1 to 18 carbons atoms or a cyclic, straight-chain or branched alkyl residue which is unsubstituted, mono- or poly-substituted by fluorine, chlorine, cyano, having 1 to 18 carbons atoms, wherein one or more non-adjacent —$CH_2$— groups is independently replaced by —O— or —CH=CH—, or $R^4$ and $R^5$ together to form a $C_{5-8}$ alicyclic ring.

18. Diamine compounds according to claim 14, wherein F is selected from the group comprising —$OR^2$ or —$NHR^3$, wherein $R^2$ and $R^3$ represent a cyclic, straight-chain or branched alkyl residue which is unsubstituted, mono- or poly-substituted by fluorine atoms, having 1 to 18 carbon atoms or a cyclic, straight-chain or branched alkyl residue which is unsubstituted, mono- or poly-substituted by fluorine atoms, having 1 to 18 carbon atoms, wherein one or more non-adjacent —$CH_2$— groups is independently replaced by —O—.

19. Diamine compounds according to claim 14, wherein G is a hydrogen atom, or fluorine atom, or chlorine atom, a straight-chain or branched alkyl group which is unsubstituted, mono-substituted by cyano, fluorine or chlorine or poly-substituted by fluorine, chlorine, having 1 to 18 carbon atoms, or a straight-chain or branched alkyl group which is unsubstituted, mono-substituted by cyano, fluorine or chlorine or poly-substituted by fluorine, chlorine, having 1 to 18 carbon atoms, wherein one or more —$CH_2$— groups is independently replaced —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C— and —O—CO—O—, an aromatic or an alicyclic group, with the proviso that oxygen atoms are not directly attached to each other, and wherein $R^1$ represents a hydrogen atom or a straight chain or branched hydrocarbon radical having from 1 to 6 carbon atoms.

20. Diamine compounds according to claim 14, wherein G is a hydrogen atom, a straight-chain or branched alkyl group having 1 to 18 carbon atoms, or a straight-chain or branched alkyl group having 1 to 18 carbon atoms, wherein one or more non-adjacent —$CH_2$— groups is independently replaced —O—, —CO—, —CO—O—, —O—CO—, —$NR^1$—, —$NR^1$—CO—, —CO—$NR^1$—, and —O—CO—O—, with the proviso that oxygen atoms are not directly attached to each other, and wherein $R^1$ represents a hydrogen atom or a straight chain or branched hydrocarbon radical having from 1 to 6 carbon atoms.

21. Diamine compounds according to claim 14, wherein $S^2$ is selected from a single covalent bond, —CO—O—, —CO—$NR^1$—, —CO—, a straight-chain or branched alkylene group which is unsubstituted, mono or poly-substituted by fluorine, chlorine, or cyano, having 1 to 24 carbon atoms, and a straight-chain or branched alkylene group which is unsubstituted, mono or poly-substituted by fluorine, chlorine, or cyano, having 1 to 24 carbon atoms, wherein one or more —$CH_2$— groups is independently replaced by a group J, with the proviso that oxygen atoms are not directly attached to each other, wherein $R^1$ represents a hydrogen atom or a straight chain or branched hydrocarbon radical having from 1 to 6 carbon atoms.

22. Diamine compounds according to claim 14, wherein $S^2$ is selected from a single covalent bond, —CO—O—, —CO—, —$(CH_2)_r$—, —$(CH_2)_r$—O—, —$(CH_2)_r$—CO—, —$(CH_2)_r$—CO—O—, —$(CH_2)_r$—O—CO—, —$(CH_2)_r$—CO—$NR^1$—, —CO—O—$(CH_2)_r$—O—, —$(CH_2)_r$—$NR^1$—CO—, —$(CH_2)_r$—$NR^1$—, —CO—O—$(CH_2)_r$—, —CO—$NR^1$—$(CH_2)_r$—, —CO—$NR^1$—$(CH_2)_r$—O—, —CO—$NR^1$—$(CH_2)_r$—$NR^1$—, —CO—$NR^1$—$(CH_2)_r$—O—CO—, —$(CH_2)_r$—O—$(CH_2)_s$—, —$(CH_2)_r$—CO—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$—CO—O—$(CH_2)_s$—, —$(CH_2)_r$—O—$(CH_2)_s$—O—, —$(CH_2)_r$—CO—O—$(CH_2)_s$—O—, —$(CH_2)_r$—$NR^1$—CO—$(CH_2)_s$—O—, —$(CH_2)_r$—$NR^1$—CO—O—$(CH_2)_s$—O—, —CO—O—$(CH_2)_r$—O—$(CH_2)_s$— and —CO—O—$(CH_2)_r$—O—$(CH_2)_s$—O—, wherein $R^1$ is as defined above, r and s each represent an integer from 1 to 20, and r+s≦21.

23. Diamine compounds according to claim 14, wherein $S^2$ is selected from a single covalent bond, —$(CH_2)_r$—, —$(CH_2)_r$—O—, —$(CH_2)_r$—CO—O—, —$(CH_2)_r$—O—CO—, —$(CH_2)_r$—CO—NH—, —$(CH_2)_r$—NH—CO—, —CO—O—$(CH_2)_r$—, —CO—NH—$(CH_2)_r$—, —CO—O—$(CH_2)_r$—O—, —CO—NH—$(CH_2)_r$—O—, —$(CH_2)_r$—NH—CO—$(CH_2)_s$—, —$(CH_2)_r$—NH—CO—O—$(CH_2)_s$—, —$(CH_2)_r$—O—$(CH_2)_s$—O—, —$(CH_2)_r$—NH—CO—$(CH_2)_s$—O—, —$(CH_2)_r$—NH—CO—O—$(CH_2)_s$—O—, —CO—O—$(CH_2)_r$—O—$(CH_2)_s$—O—, and —CO—$(CH_2)_r$—NH—CO—$(CH_2)_s$—O—, wherein r and s each represent an integer from 1 to 12 and r+s≦15.

24. Diamine compounds according to claim 14, wherein $S^2$ include 1,2-ethylen, 1,3-propylen, 1,4-butylen, 1,5-pentylen, 1,6-hexylen, 1,7-heptylen, 1,8-octylen, 1,9-nonylen, 1,10-decylen, 1,11-undecylen, 1,12-dodecylen, 3-methyl-1,4-butylen, 2-(methylenoxy)ethylen, 3-(methylenoxy)propylen, 4-(methylenoxy)butylen, 5-(methylenoxy)pentylen, 6-(methylenoxy)hexylen, 7-(methylenoxy)heptylen, 8-(methylenoxy)octylen, 9-(methylenoxy)nonylen, 10-(methylenoxy)decylen, 11-(methylenoxy)undecylen, 12-(methylenoxy)dodecylen, 2-(carbonyloxy)ethylen, 3-(carbonyloxy)propylen, 4-(carbonyloxy)butylen, 5-(carbonyloxy)pentylen, 6-(carbonyloxy)hexylen, 7-(carbonyloxy)heptylen, 8-(carbonyloxy)octylen, 9-(carbonyloxy)nonylen, 10-(carbonyloxy)decylen, 11-(carbonyloxy)undecylen, 12-(carbonyloxy)dodecylen, 2-(carbonylamino)ethylen, 3-(carbonylamino)propylen, 4-(carbonylamino)butylen, 5-(carbonylamino)pentylen, 6-(carbonylamino)hexylen, 7-(carbonylamino)heptylen, 8-(carbonylamino)octylen, 9-(carbonylamino)nonylen, 10-(carbonylamino)decylen, 11-(carbonylamino)undecylen, 12-(carbonylamino)dodecylen, 3-propylenoxy, 3-propylenoxycarbonyl, 2-ethylenoyloxy, 4-butylenoxy, 4-butylenoxycarbonyl, 3-propylenoyloxy, 5-pentylenoxy, 5-pentylenoxycarbonyl, 4-butylenoyloxy, 6-hexylenoxy, 6-hexylenoxycarbonyl, 5-pentylenoyloxy, 7-heptylenoxy, 7-heptylenoxycarbonyl, 6-hexylenoyloxy, 8-octylenoxy, 8-octylenoxycarbonyl, 7-heptylenoyloxy, 9-nonylenoxy, 9-nonylenoxycarbonyl, 8-octylenoyloxy, 10-decylenoxy, 10-decylenoxycarbonyl, 9-nonylenoyloxy, 11-undecylenoxy, 11-undecylenoxycarbonyl, 10-decylenoyloxy, 12-dodecylenoxy, 12-dodecylenoxycarbonyl, 11-undecylenoyloxy, 3-propylenaminocarbonyl, 4-butylenaminocarbonyl, 5-pentylenaminocarbonyl, 6-hexylenaminocarbonyl, 7-heptylenaminocarbonyl, 8-octylenaminocarbonyl, 9-nonylenaminocarbonyl, 10-decylenaminocarbonyl, 11-undecylenaminocarbonyl, 12-dodecylenaminocarbonyl, 2-ethylenoylamino, 3-propylenoylamino, 4-butylenoylamino, 5-pentylenoylamino, 6-hexylenoylamino, 7-heptylenoylamino, 8-octylenoylamino, 9-nonylenoylamino, 10-decylenoylamino, 11-undecylenoylamino, 2-(methylenoxy)ethanoyloxy, 3-(methylenoxy)propyloxy, 3-(methylenoxy)propyloxycarbonyl, 4-(methylenoxy)butyloxy, 4-(methylenoxy)butyloxycarbonyl, 3-(methylenoxy)propanoyloxy, 5-(methylenoxy)pentyloxy, 5-(methylenoxy)pentyloxycarbonyl, 4-(methylenoxy)butanoyloxy, 6-(methylenoxy)hexyloxy, 6-(methylenoxy)hexyloxycarbonyl, 5-(methylenoxy)pentanoyloxy, 7-(methylenoxy)heptyloxy, 7-(methylenoxy)heptyloxycarbonyl, 6-(methylenoxy)hexanoyloxy, 8-(methylenoxy)octyloxy, 8-(methylenoxy)octyloxycarbonyl, 7-(methylenoxy)heptanoyloxy, 9-(methylenoxy)nonyloxy, 9-(methylenoxy)nonyloxycarbonyl, 8-(methylenoxy)octanoyloxy, 10-(methylenoxy)decyloxy, 10-(methylenoxy)decyloxycarbonyl, 9-(methylenoxy)nonanoyloxy, 11-(methylenoxy)undecyloxy, 11-(methylenoxy)undecyloxycarbonyl, 10-(methylenoxy)decanoyloxy, 12-(methylenoxy)dodecyloxy, 12-(methylenoxy)dodecyloxycarbonyl, 11-(methylenoxy)undecanoyloxy, 3-(methylenoxy)propylaminocarbonyl, 4-(methylenoxy)butylaminocarbonyl, 5-(methylenoxy)pentylaminocarbonyl, 6-(methylenoxy)hexylaminocarbonyl, 7-(methylenoxy)heptylaminocarbonyl, 8-(methylenoxy)octylaminocarbonyl, 9-(methylenoxy)nonylaminocarbonyl, 10-(methylenoxy)decylaminocarbonyl, 11-(methylenoxy)undecylaminocarbonyl, 12-(methylenoxy)dodecylaminocarbonyl, 2-(methylenoxy)ethanoylamino, 3-(methylenoxy)propanoylamino, 4-(methylenoxy)butanoylamino, 5-(methylenoxy)pentanoylamino, 6-(methylenoxy)hexanoylamino, 7-(methylenoxy)heptanoylamino, 8-(methylenoxy)octanoylamino, 9-(methylenoxy)nonanoylamino, 10-(methylenoxy)decanoylamino, 11-(methylenoxy)undecanoylamino, 12-(methylenoxy)dodecylaminocarbonyl, 2-(carbonyloxy)ethanoyloxy, 3-(carbonyloxy)propyloxy, 3-(carbonyloxy)propyloxycarbonyl, 4-(carbonyloxy)butyloxy, 4-(carbonyloxy)butyloxycarbonyl, 3-(carbonyloxy)propanoyloxy, 5-(carbonyloxy)pentyloxy, 5-(carbonyloxy)pentyloxycarbonyl, 4-(carbonyloxy)butanoyloxy, 6-(carbonyloxy)hexyloxy, 6-(carbonyloxy)hexyloxycarbonyl, 5-(carbonyloxy)pentanoyloxy, 7-(carbonyloxy)heptyloxy, 7-(carbonyloxy)heptyloxycarbonyl, 6-(carbonyloxy)hexanoyloxy, 8-(carbonyloxy)octyloxy, 8-(carbonyloxy)octyloxycarbonyl, 7-(carbonyloxy)heptanoyloxy, 9-(carbonyloxy)nonyloxy, 9-(carbonyloxy)nonyloxycarbonyl, 8-(carbonyloxy)octanoyloxy, 10-(carbonyloxy)decyloxy, 10-(carbonyloxy)decyloxycarbonyl, 9-(carbonyloxy)nonanoyloxy, 11-(carbonyloxy)undecyloxy, 11-(carbonyloxy)undecyloxycarbonyl, 10-(carbonyloxy)decanoyloxy, 12-(carbonyloxy)dodecyloxy, 12-(carbonyloxy)dodecyloxycarbonyl, 11-(carbonyloxy)undecanoyloxy, 3-(carbonyloxy)propylaminocarbonyl, 4-(carbonyloxy)butylaminocarbonyl, 5-(carbonyloxy)pentylaminocarbonyl, 6-(carbonyloxy)hexylaminocarbonyl, 7-(carbonyloxy)heptylaminocarbonyl, 8-(carbonyloxy)octylaminocarbonyl, 9-(carbonyloxy)nonylaminocarbonyl, 10-(carbonyloxy)decylaminocarbonyl, 11-(carbonyloxy)undecylaminocarbonyl, 12-(carbonyloxy)dodecylaminocarbonyl, 2-(carbonyloxy)ethanoylamino, 3-(carbonyloxy)propanoylamino, 4-(carbonyloxy)butanoylamino, 5-(carbonyloxy)pentanoylamino, 6-(carbonyloxy)hexanoylamino, 7-(carbonyloxy)heptanoylamino, 8-(carbonyloxy)octanoylamino, 9-(carbonyloxy)nonanoylamino, 10-(carbonyloxy)decanoylamino, 11-(carbonyloxy)undecanoylamino, 12-(carbonyloxy)dodecylaminocarbonyl, 6-(3-propylenaminocarbonyloxy)hexylen, 6-(3-propylenoxy)hexylen, 6-(3-propylenoxy)hexyloxy, 6-(3-propylenaminocarbonyloxy)hexyloxy, 6-(3-propylenaminocarbonyl)hexyl, 6-(3-propylenaminocarbonyl)hexyloxy, 2-(methylenoxy)ethyloxycarbonyloxy, 3-(methylenoxy)propyloxycarbonyloxy, 6-(methylenoxy)hexyloxycarbonyloxy, 2-(methylenoxycarbonyl)ethylen, 3-(methylenoxycarbonyl)propyloxycarbonyloxy, 6-(methylenoxycarbonyl)hexyloxycarbonyloxy, 6-(3-propylenoxycarbonyloxy)hexylen, 6-(3-propylenoxycarbonyl)hexylen, 2-(methylenaminocarbonyl)ethylen, 3-(methylenaminocarbonyl)propylen, 6-(methylenaminocarbonyl)hexylen, 6-(3-propylenaminocarbonyloxy)hexylen, 6-(3-propylenaminocarbonyl)hexylen, 4-{[6-{methylenoxy}hexyl]oxy}phenylen, 4-[6-(methylenoxy)hexyl]cyclohexylen, 3-methoxy-4-{[6-(methylenoxy)hexyl]oxy}phenylen, 4-{[6-(methylenoxy)hexyl]oxy}phenylcarbonyloxy, 4-[6-(methylenoxy)hexyl]cyclohexanoyloxy, 3-ethoxy-4-{[8-(methylenoxy)octyl]oxy}phenylcarbonyloxy, 4-[3-(carbonyloxy)propyl]phenylen, 4-[6-(carbonyloxy)hexyl]phenylen, 4-[6-(carbonyloxy)hexyl]cyclohexylen, 3-methoxy-4-[6-(carbonyloxy)hexyl]phenylen, 4-[6-(carbonyloxy)hexyl]phenylcarbonyloxy, 4-[6-(carbonyloxy)hexyl]cyclohexanoyloxy, 3-ethoxy-4-[8-(carbonyloxy)octyl]phenylcarbonyloxy, 2-{4-4-{2-(methylenoxy)ethyl}cyclohexyl]phenyl}ethoxy, 1-[4'-{[4-(methylenoxy)butyl]oxy}-1,1'biphenyl-4-yl]carbonyloxy, 1-{4-[4-{2-(methylenoxy)ethoxy}phenyl}methyloxy, 2-{4-[4-(2-carbonyloxyethyl)cyclohexyl]phenyl}ethoxy, 2-[4'-(4-carbonyloxybutyl)-1,1'-biphenylen-4-yl]ethoxy, 6-{4-[4-(2-carbonyloxyethyl)phenyl}hexyloxy, and 5-{[4'-[4-(methylenoxy)butoxy)]-1,1'-biphenyl-4-yl]oxy}pentanoyloxy.

25. Diamine compounds according to claim 14, wherein $S^3$ is selected from —CO—O—, —CO—NR$^1$—, —CO—, a straight-chain or branched alkylene group which is unsubstituted, mono or poly-substituted by fluorine, chlorine, or cyano, having 1 to 24 carbon atoms, and a straight-chain or branched alkylene group which is unsubstituted, mono or poly-substituted by fluorine, chlorine, or cyano, having 1 to 24 carbon atoms, wherein one or more —CH$_2$— groups is independently replaced by a group J, with the proviso that oxygen atoms are not directly attached to each other, wherein R$^1$ represents a hydrogen atom or a straight chain or branched hydrocarbon radical having from 1 to 6 carbon atoms.

26. Diamine compounds according to claim 14, wherein $S^3$ is selected from a single covalent bond, —(CH$_2$)$_r$—, —CO—(CH$_2$)$_r$—, —CO—O—(CH$_2$)$_r$—, —CO—NR$^1$—(CH$_2$)$_r$—, —(CH$_2$)$_r$—O—(CH$_2$)$_s$—, —(CH$_2$)$_r$—CO—O—(CH$_2$)$_s$—, —(CH$_2$)$_r$—O—CO—(CH$_2$)$_s$—, —(CH$_2$)$_r$NR$^1$—CO—(CH$_2$)$_s$—, —(CH$_2$)$_r$—NR$^1$—CO—O—(CH$_2$)$_s$—, and —CO—O—(CH$_2$)$_r$—O—(CH$_2$)$_s$—, wherein R$^1$ is as defined herein above; r and s each represent an integer from 1 to 20; and r+s≦21.

27. Diamine compounds according to claim 14, wherein $S^3$ include 1,2-ethylen, 1,3-propylen, 1,4-butylen, 1,5-pentylen, 1,6-hexylen, 1,7-heptylen, 1,8-octylen, 1,9-nonylen, 1,10-decylen, 1,11-undecylen, 1,12-dodecylen, 3-methyl-1,4-butylen, 2-(methylenoxy)ethylen, 3-(methylenoxy)propylen, 4-(methylenoxy)butylen, 5-(methylenoxy)pentylen, 6-(methylenoxy)hexylen, 7-(methylenoxy)heptylen, 8-(methylenoxy)octylen, 9-(methylenoxy)nonylen, 10-(methylenoxy)decylen, 11-(methylenoxy)undecylen, 12-(methylenoxy)dodecylen, 2-(carbonyloxy)ethylen, 3-(carbonyloxy)propylen, 4-(carbonyloxy)butylen, 5-(carbonyloxy)pentylen, 6-(carbonyloxy)hexylen, 7-(carbonyloxy)heptylen, 8-(carbonyloxy)octylen, 9-(carbonyloxy)nonylen, 10-(carbonyloxy)decylen, 11-(carbonyloxy)undecylen, 12-(carbonyloxy)dodecylen, 2-(carbonylamino)ethylen, 3-(carbonylamino)propylen, 4-(carbonylamino)butylen, 5-(carbonylamino)pentylen, 6-(carbonylamino)hexylen, 7-(carbonylamino)heptylen, 8-(carbonylamino)octylen, 9-(carbonylamino)nonylen, 10-(carbonylamino)decylen, 11-(carbonylamino)undecylen, 12-(carbonylamino)dodecylen, 6-(3-propylenaminocarbonyloxy)hexylen, 6-(3-propylenoxy)hexylen, 6-(3-propylenaminocarbonyl)hexyl, 2-(methylenoxycarbonyl)ethylen, 6-(3-propylenoxycarbonyloxy)hexylen, 6-(3-propylenoxycarbonyl)hexylen, 2-(methylenaminocarbonyl)ethylen, 3-(methylenaminocarbonyl)propylen, 6-(methylenaminocarbonyl)hexylen, 6-(3-propylenaminocarbonyloxy)hexylen, 6-(3-propylenaminocarbonyl)hexylen, 4-{[6-(methylenoxy)hexyl]oxy}phenylen, 4-1,6-(methylenoxy)hexyl]cyclohexylen, 3-methoxy-4-{[6-(methylenoxy)hexyl]oxy}phenylen, 4-[3-(carbonyloxy)propyl]phenylen, 4-[6-(carbonyloxy)hexyl]phenylen, and 4-[6-(carbonyloxy)hexyl]cyclohexylen, 3-methoxy-4-[6-(carbonyloxy)hexyl]phenylen.

28. Diamine compounds according to claim 14, wherein Q is an oxygen atom or —NH—.

29. Diamine compounds according to claim 14, wherein Q is an oxygen atom.

30. Diamine compounds according to claim 14, wherein X and Y represent hydrogen.

31. Diamine compounds according to claim 14, wherein the photoactive groups are groups of formula IIIa.

32. Method of using a diamine compound according to claim 14, comprising providing the diamine compound as precursor for the production of liquid crystal alignment layers.

33. A liquid crystal orientation material obtained by the reaction of a diamine compound represented by the general formula I:

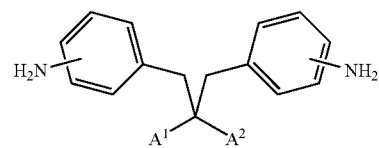

wherein $A^1$ and $A^2$ each independently represent a mesogen group represented by general formula II:

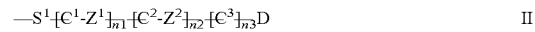

wherein $C^1$ to $C^3$ each independently represent an aromatic or an alicyclic group, which is unsubstituted or mono- or poly-substituted by a cyano group or by halogen atoms, or by a cyclic, straight-chain or branched alkyl residue which is unsubstituted, mono- or poly-substituted by fluorine, chlorine, having 1 to 18 carbon atoms, or by a cyclic, straight-chain or branched alkyl residue which is unsubstituted, mono- or poly-substituted by fluorine, chlorine, having 1 to 18 carbon atoms, wherein one or more non-adjacent —CH$_2$— groups is independently replaced by a group B;

D represents a hydrogen atom, a halogen atom, a cyano group, or a straight-chain or branched alkyl residue which is unsubstituted, mono-substituted by cyano or fluorine, chlorine, or poly-substituted by fluorine, chlorine, having 1 to 24 carbon atoms, or a straight-chain or branched alkyl residue which is unsubstituted, mono-substituted by cyano or fluorine, chlorine, or poly-substituted by fluorine, chlorine, having 1 to 24 carbon atoms, wherein one or more non-adjacent —CH$_2$— groups is independently replaced by a group B, or represents a organic group having a steroid skeleton;

$S^1$ represents 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 2-(methylenoxy)ethylene, 3-(methylenoxy)propylene, 4-(methylenoxy)butylene, 5-(methylenoxy)pentylene, 6-(methylenoxy)hexylene, 7-(methylenoxy)heptylene, 8-(methylenoxy)octylene, 9-(methylenoxy)nonylene, 10-(methylenoxy)decylene, 11-(methylenoxy)undecylene, 12-(methylenoxy)dodecylene, 2-(carbonyloxy)ethylene, 3-(carbonyloxy)propylene, 4-(carbonyloxy)butylene, 5-(carbonyloxy)pentylene, 6-(carbonyloxy)hexylene, 7-(carbonyloxy)heptylene, 8-(carbonyloxy)octylene, 9-(carbonyloxy)nonylene, 10-(carbonyloxy)decylene, 11-(carbonyloxy)undecylene, 12-(carbonyloxy)dodecylene, 2-(carbonylamino)ethylene, 3-(carbonylamino)propylene, 4-(carbonylamino)butylene, 5-(carbonylamino)pentylene, 6-(carbonylamino)hexylene, 7-(carbonylamino)heptylene, 8-(carbonylamino)octylene, 9-(carbonylamino)nonylene, 10-(carbonylamino)decylene, 11-(carbonylamino)undecylene, 12-(carbonylamino)dodecylene, 3-propyleneoxy, 3-propyleneoxycarbonyl, 2-ethylenoyloxy, 4-butyleneoxy, 4-butyleneoxycarbonyl, 3-propylenoyloxy, 5-pentyleneoxy, 5-pentyleneoxycarbonyl, 4-butylenoyloxy, 6-hexyleneoxy, 6-hexyleneoxycarbonyl, 5-pentylenoyloxy, 7-heptyleneoxy, 7-heptyleneoxycarbonyl, 6-hexylenoyloxy, 8-octyleneoxy, 8-octyleneoxycarbonyl, 7-heptylenoyloxy, 9-nonyleneoxy, 9-nonyleneoxycarbonyl, 8-octylenovioxy, 10-decyleneoxy, 10-decyleneoxycarbonyl, 9-nonylenoyloxy, 11-undecyleneoxy, 11-undecyleneoxycarbonyl, 10-decylenoyloxy, 12-dodecyleneoxy, 12-dodecyleneoxycarbonyl, 11-undecylenoyloxy, 3-propyleneaminocarboflyl, 4-butyleneaminocarbonyl, 5-pentyleneaminocarbonyl, 6-hexyleneaminocarbonyl, 7-heptyleneaminocarbonyl, 8-octyleneaminocarbonyl, 9-nonyleneaminocarbonyl, 10-decyleneaminocarbonyl, 11-undecyleneaminocarbonyl, 12-dodecyleneaminocarbonyl, 2-ethylenecarbonylamino, 3-propylenecarbonylamino, 4-butylenecarbonylamino, 5-pentylenecarbonylamino, 6-hexylenecarbonylamino, 7-heptylenecarbonylamino, 8-octylenecarbonylamino, 9-nonylenecarbonylamino, 10-decylenecarbonylamino, 11-undecylenecarbonylamino, 2-(methylenoxy)ethanoyloxy, 3-(methylenoxy)propyloxy, 3-(methylenoxy)propyloxycarbonyl, 4-(methylenoxy)butyloxy, 4-(methylenoxy)butyloxycarbonyl, 3-(methylenoxy)propanoyloxy, 5-(methylenoxy)pentyloxy, 5-(methylenoxy)pentyloxycarbonyl, 4-(methylenoxy)butanoyloxy, 6-(methylenoxy)hexyloxy, 6-(methylenoxy)hexyloxycarbonyl, 5-(methylenoxy)pentanoyloxy, 7-(methylenoxy)heptyloxy, 7-(methylenoxy)heptyloxycarbonyl, 6-(methylenoxy)hexanoyloxy, 8-(methylenoxy)octyloxy, 8-(methylenoxy)octyloxycarbonyl, 7-(methylenoxy)heptanoyloxy, 9-(methylenoxy)nonyloxy, 9-(methylenoxy)nonyloxycarbonyl, 8-(methylenoxy)octanoyloxy, 10-(methylenoxy)decyloxy, 10-(methylenoxy)decyloxycarbonyl, 9-(methylenoxy)nonanoyloxy, 11-(methylenoxy)undecyloxy, 11-(methylenoxy)undecyloxycarbonyl, 10-(methylenoxy)decanoyloxy, 12-(methylenoxy)dodecyloxy, 12-(methylenoxy)dodecyloxycarbonyl, 11-(methylenoxy)undecanoyloxy, 3-(methylenoxy)propylaminocarbonyl, 4-(methylenoxy)butylaminocarbonyl, 5-(methylenoxy)pentylaminocarbonyl, 6-(methylenoxy)hexylaminocarbonyl, 7-(methylenoxy)heptylaminocarbonyl, 8-(methylenoxy)octylaminocarbonyl, 9-(methylenoxy)nonylaminocarbonyl, 10-(methylenoxy)decylaminocarbonyl, 11-(methylenoxy)undecylaminocarbonyl, 12-(methylenoxy)dodecylaminocarbonyl, 2-(methylenoxy)ethanoylamino, 3-(methylenoxy)propanoylamino, 4-(methylenoxy)butanoylamino, 5-(methylenoxy)pentanoylamino, 6-(methylenoxy)hexanoylamino, 7-(methylenoxy)heptanoylamino, 8-(methylenoxy)octanoylamino, 9-(methylenoxy)nonanoylamino, 10-(methylenoxy)decanoylamino, 11-(methylenoxy)undecanoylamino, 12-(methylenoxy)dodecylaminocarbonyl, 2-(carbonyloxy)ethanoyloxy, 3-(carbonyloxy)propyloxy, 3-(carbonyloxy)propyloxycarbonyl, 4-(carbonyloxy)butyloxy, 4-(carbonyloxy)butyloxycarbonyl, 3-(carbonyloxy)propanoyloxy, 5-(carbonyloxy)pentyloxy, 5-(carbonyloxy)pentyloxycarbonyl, 4-(carbonyloxy)butanoyloxy, 6-(carbonyloxy)hexyloxy, 6-(carbonyloxy)hexyloxycarbonyl, 5-(carbonyloxy)pentanoyloxy, 7-(carbonyloxy)heptyloxy, 7-(carbonyloxy)heptyloxycarbonyl, 6-(carbonyloxy)hexanoyloxy, 8-(carbonyloxy)octyloxy, 8-(carbonyloxy)octyloxycarbonyl, 7-(carbonyloxy)heptanoyloxy, 9-(carbonyloxy)nonyloxy, 9-(carbonyloxy)nonyloxycarbonyl, 8-(carbonyloxy)octanoyloxy, 10-(carbonyloxy)decyloxy, 10-(carbonyloxy)decyloxycarbonyl, 9-(carbonyloxy)nonanoyloxy, 11-(carbonyloxy)undecyloxy, 11-(carbonyloxy)undecyloxycarbonyl, 10-(carbonyloxy)decanoyloxy, 12-(carbonyloxy)dodecyloxy, 12-(carbonyloxy)dodecyloxycarbonyl, 11-(carbonyloxy)undecanoyloxy, 3-(carbonyloxy)propylaminocarbonyl, 4-(carbonyloxy)butylaminocarbonyl, 5-(carbonyloxy)pentylaminocarbonyl, 6-(carbonyloxy)hexylaminocarbonyl, 7-(carbonyloxy)heptylaminocarbonyl, 8-(carbonyloxy)octylaminocarbonyl, 9-(carbonyloxy)nonylaminocarbonyl, 10-(carbonyloxy)decylaminocarbonyl, 11-(carbonyloxy)undecylaminocarbonyl, 12-(carbonyloxy)dodecylaminocarbonyl, 2-(carbonyloxy)ethanoylamino, 3-(carbonyloxy)propanoylamino, 4-(carbonyloxy)butanoylamino, 5-(carbonyloxy)pentanoylamino, 6-(carbonyloxy)hexanoylamino, 7-(carbonyloxy)heptanoylamino, 8-(carbonyloxy)octanoylamino, 9-(carbonyloxy)nonanoylamino, 10-(carbonyloxy)decanoylamino, 11-(carbonyloxy)undecanoylamino, 12-(carbonyloxy)dodecylaminocarbonyl 6-(3-propyleneaminocarbonyloxy)hexylene, 6-(3-propyleneoxy)hexylene, 6-(3-propyleneoxy)hexyloxy, 6-(3-propyleneaminocarbonyloxy)hexyloxy, 6-(3-propyleneaminocarbonyl)hexyl, 6-(3-propyleneaminocarbonyl)hexyloxy, 2-(1-methyleneoxy)ethyloxycarbonyloxy, 3-(1-methyleneoxy)propyloxycarbonyloxy, 6-(1-methyleneoxy)hexyloxycarbonyloxy, 2-(1-methyleneoxycarbonyl)ethylene, 3-(1-methyleneoxycarbonyl)propyloxycarbonyloxy, 6-(1-methyleneoxycarbonyl)hexyloxycarbonyloxy, 6-(3-propyleneoxycarbonyloxy)hexylene, 6-(3-propyleneoxycarbonyl)hexylene, 2-(1-methyleneaminocarbonyl)ethylene, 3-(1-methyleneaminocarbonyl)propylene, 6-(1-methyleneaminocarbonyl)hexylene, and 6-(3-propyleneaminocarbonyloxy)hexylene, 6-(3-propyleneaminocarbonyl)hexylene;

$Z_1$, $Z_2$ each independently of the other represent a single bond or a spacer unit which is straight-chain or branched alkylene group which is unsubstituted, mono or polysubstituted by a cyano group or by halogen atoms, having 1 to 8 carbon atoms or a spacer unit such a straight-chain or branched alkylene group which is unsubstituted, mono or poly-substituted by a cyano group or by halogen atoms, having 1 to 8 carbon atoms, wherein one or more non-adjacent —$CH_2$— groups is independently replaced by a group B;

$n_1$ is 0 or 1, and $n_2$ and $n_3$ are 1; and

B represents a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O— and —Si($CH_3$)$_2$—O—Si($CH_3$)$_2$— and wherein $R^1$ represents a hydrogen atom or a straight chain or branched hydrocarbon radical having from 1 to 6 carbon atoms.

\* \* \* \* \*